United States Patent [19] [11] Patent Number: 4,915,102
Kwiatek et al. [45] Date of Patent: Apr. 10, 1990

[54] HINGED DERMAL APPLICATOR

[75] Inventors: Alfred Kwiatek, Swanton; John J. Wick, Williston, both of Vt.

[73] Assignee: Bertek, Inc., Swanton, Vt.

[21] Appl. No.: 239,592

[22] Filed: Sep. 1, 1988

[51] Int. Cl.⁴ .............................................. A61L 15/00
[52] U.S. Cl. .................................. 128/156; 128/155; 206/440; 206/441
[58] Field of Search ................ 128/155, 156; 206/439, 206/440, 441, 442

[56] References Cited

U.S. PATENT DOCUMENTS

| | | | |
|---|---|---|---|
| 3,017,990 | 1/1962 | Singerman | 206/440 |
| 3,899,077 | 8/1975 | Spiegelberg | 206/441 |
| 4,304,333 | 12/1981 | Kozlow Sr. | 206/441 |
| 4,549,653 | 10/1985 | Lauritzen | 206/440 X |
| 4,664,106 | 5/1987 | Snedelcer | 128/156 |
| 4,706,662 | 11/1987 | Thompson | 128/156 X |
| 4,738,257 | 4/1988 | Meyer et al. | 128/156 |
| 4,742,826 | 5/1988 | McLorg | 128/155 X |
| 4,744,355 | 5/1988 | Faasse Jr. | 128/156 |
| 4,781,293 | 11/1988 | Johns | 128/156 X |

Primary Examiner—V. Millin
Assistant Examiner—N. Paul
Attorney, Agent, or Firm—Lerner, David, Littenberg, Krumholz & Mentlik

[57] ABSTRACT

Devices for applying film layers and/or active agent carriers to the skin are disclosed, including a liner layer having a release surface, a carrier layer for the film layer, a first adhesive between the carrier layer and the film layer, and a second adhesive between the liner layer and the opposite surface of the film layer and carrier layer. In this manner, the film layer is sandwiched between the liner layer and carrier layer, and the coefficients of adhesion of the two adhesives are selected so that upon separation of the liner layer and the carrier layer the film layer remains on the carrier layer, and upon application of the film layer to the skin, the film layer transfers from the carrier layer to the skin. The device preferably includes a hinge permanently connecting a peripheral edge of the carrier layer to the liner layer in order to facilitate this process, and in a preferred embodiment an active agent carrier is either substituted for or added to the film layer.

153 Claims, 9 Drawing Sheets

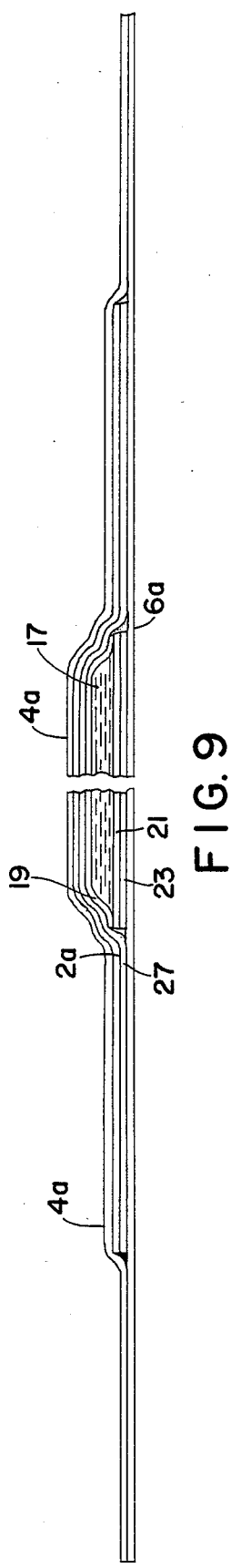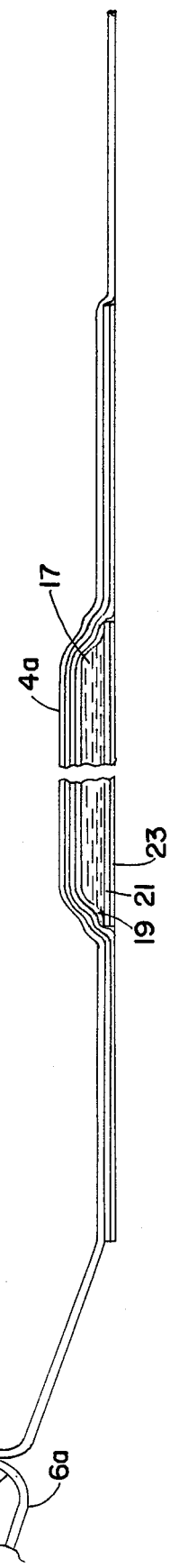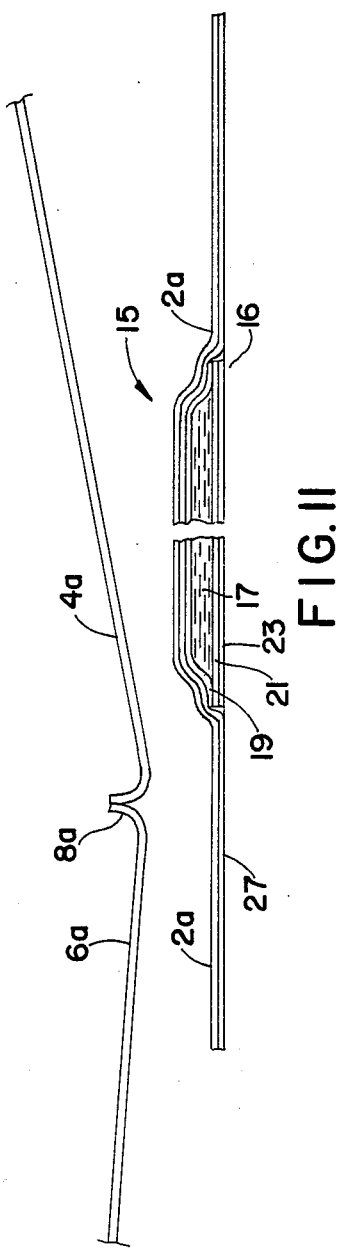

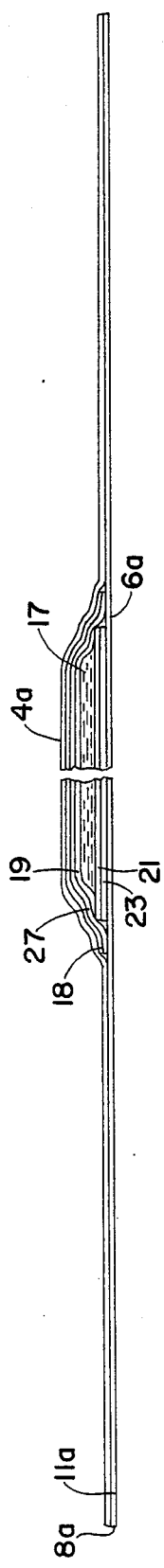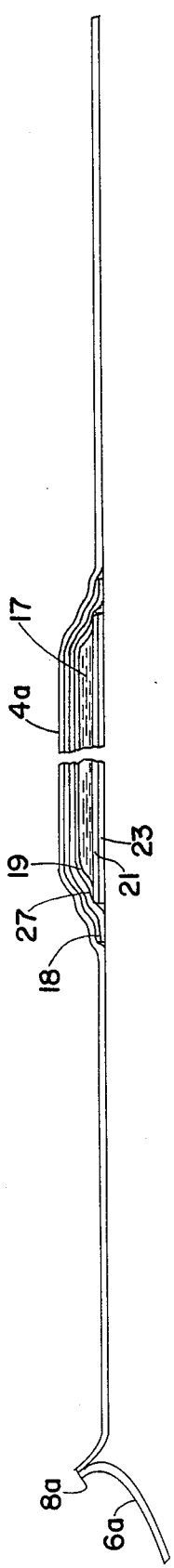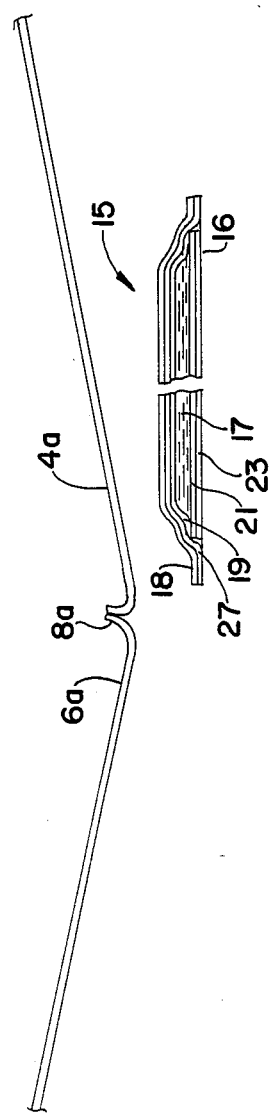

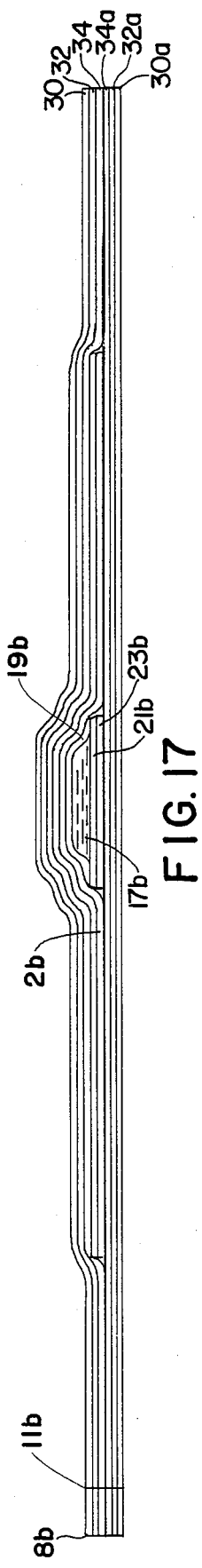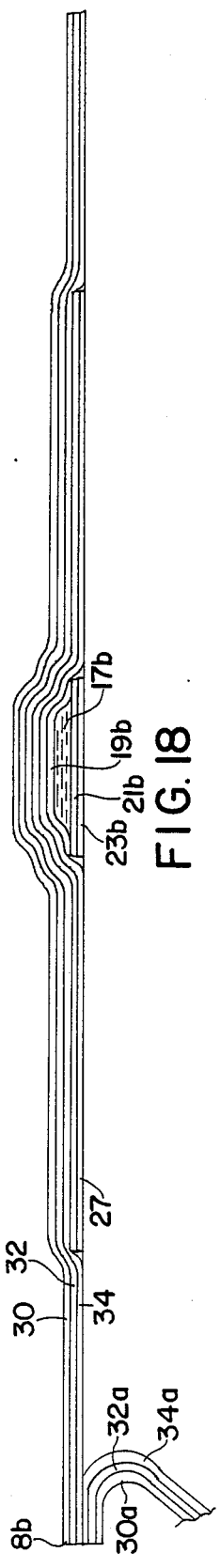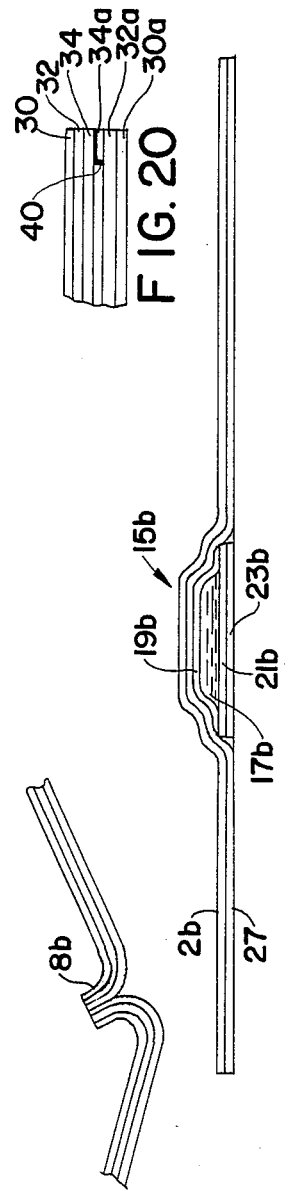

HINGED DERMAL APPLICATOR

FIELD OF THE INVENTION

The present invention relates to the application of film layers to the skin or mucosa of a patient. More particularly, the present invention relates to devices for the handling of film layers to be applied to the skin of mucosa of a patient. Still more particularly, the present invention relates to the application of devices for the administration of an active agent to a host. Still more particularly, the present invention relates to the application of devices allowing for the topical administration to the host or administration through the skin or mucosa of the host over a period of time. Even more particularly, the present invention relates to devices for applying such devices to the skin or mucosa of a patient.

BACKGROUND OF THE INVENTION

There has been considerable effort to develop various devices which include film layers which are ultimately to be applied to the skin of a host or patient. These various devices include, for example, bandages which are in the form of a film and can be substituted for conventional bandages.

By way of background, it should thus be understood that for centuries the common understanding of wound healing and treatment remained relatively static. There was a general understanding based on experience that open wounds were subject to contamination and infection. Beyond that, there was a perception that optimum healing occurred under the natural protective cover of dried wound exudate—a scab. As a result, dressing materials, typically composed of gauze or fabric, were used over both traumatic and surgical wounds to protect them from gross particulate contamination and to promote drying and scab formation.

Not until the early 1970's was it observed and published that, contrary to long established thought, wounds do in fact heal significantly faster and with less scar formation under a film which maintains a well-balanced moist environment, such as that which naturally occurs under a blister.

This changed perception of the wound healing process, along with a widespread recognition of its commercial implications, led to the introduction beginning in 1981 of a new category of "moist environment" synthetic transparent adhesive dressings based on adhesive coated films extruded or cast from high moisture vapor permeable, elastomeric resins—initially polyurethanes. In the several years since their commercial introduction, these products have achieved the acceptance of the medical community based on both clinical performance and cost effectiveness.

An example of an adhesive medical or surgical dressing which includes a moisture-vapor-permeable pressure-sensitive adhesive material is disclosed in Hodgson, U.S. Pat. Nos. Re. 31,886 and 31,887. The adhesive medical or surgical dressing is specifically shown in FIG. 5 of these patents, and includes a dressing pad 18 on the adhesive side thereof. There are also a number of wound dressing products currently on the market. These include products such as wound dressings being sold by Ferris corporation of Burr Ridge, Ill., under the mark DYNAMERM TM, which includes a backing layer, a liner layer, and a film layer therebetween within a sealed, tearable package. In this case, color-coded paper tabs are provided on either end of the carrier layer so that by pulling on a first such tab the carrier layer and the film layer are removed from the backing layer. The film can then be applied by pulling on the second tab after application to the skin. Removal of each tab, initiation of each step in this procedure, and assurance of a smooth transfer of the film cannot be guaranteed with this product, however. Other such wound dressings include products of The Kendall Company of Boston, Mass., sold under the mark POLYSKIN TM, and Johnson & Johnson sold under the mark BIOCLUSIVE. Again, none of these products can easily and rapidly apply a film layer to the skin, and in particular they do not include any hinge means between the outer layers thereof.

There have also been considerable developments in connection with transdermal administration systems. These include Ciba-Geigy's TRANSDERM®-NITRO and TRANSDERM®-V systems which have been approved for transdermal administration of nitroglycerine and scopolamine, respectively. These prior devices for the controlled, continuous metering of drugs and the like include a reservoir for the drug as well as a permeable adhesive layer for maintaining the transdermal patch or the like on the skin or mucosa of a patient. A significant improvement in this field is represented by U.S. Pat. No. 4,573,996, which is seepage-resistant during use and thus eliminates prior problems of contamination which were previously encountered with such devices.

A continuing problem with such devices, however, relates to the overall handling of these patches, and more particularly to the need to maintain the transdermal patches in contact with the skin for extended periods of time. In such situations, even where highly effective adhesives are utilized, there remains a tendency for the adhesive to become less effective with time and use, and for the patch to eventually fall off. Furthermore, it is difficult to transfer the patch without reducing its effectiveness.

The search has therefore continued for more effective systems for applying film layers to the skin or mucosa of a patient, and for applying transdermal patches and the like to the skin of a patient.

SUMMARY OF THE INVENTION

In accordance with the present invention, these and other objects have now been accomplished by the applicants' invention of a device for applying a film layer to the skin or mucosa of a patient comprises a liner layer including a first surface and a second surface, the first surface comprising a releasable surface, a carrier layer for the film layer, the carrier layer including a first surface and a second surface, hinge means permanently affixing the first surface of the liner layer to the first surface of the carrier layer at a predetermined location thereon, the film layer being located on the first surface of the carrier layer at a location displaced from the hinge means, a first adhesive layer interposed between the first surface of the carrier layer and the film layer for maintaining the film layer in contact with the carrier layer when the portion of the carrier layer other than the hinge means is separated from the liner layer, and a second adhesive layer interposed between the first surface of the liner layer and the first surface of the carrier layer which includes the film layer, for releasably maintaining the first surface of the carrier layer which includes the film layer in contact with the first surface of the liner layer, the second adhesive layer covering at least the entire periphery of the film layer, the first adhesive layer having a first coefficient of adhesion and the second adhesive layer having a second coefficient of adhesion, the first coefficient of adhesion of the carrier layer to said film layer being less than the second coefficient of adhesion of the film layer to the skin or mucosa of said patient, whereby upon application of the film layer to the skin with the second adhesive layer therebetween, the film layer adheres to the skin and the film layer can simultaneously be removed from the carrier layer.

In accordance with one embodiment of this device of the present invention, the second adhesive layer covers at least the entire surface of the film layer.

In accordance with another embodiment of this device of the present invention, the hinge means comprises a portion of the liner layer corresponding to the predetermined location which is free of the releasable surface, and including adhesive hinge means interposed between the liner layer and the carrier layer at that predetermined location.

In accordance with another embodiment of the present invention, a device has been provided for applying an active agent carrier to the skin or mucosa of a patient comprising a liner layer including a first surface and a second surface, the first surface comprising a releasable surface, a carrier layer for the active agent carrier, the carrier layer including a first surface and a second surface, the active agent carrier being located on the first surface of the carrier layer, first adhesive means interposed between the first surface of the carrier layer and the active agent carrier for maintaining the active agent carrier in contact with the carrier layer when the carrier layer is separated from the liner layer, and second adhesive means interposed between the first surface of the liner layer and the first surface of the carrier layer including the active agent carrier, for releasably maintaining the first surface of the carrier layer including the active agent carrier in contact with the first surface of the liner layer, the second adhesive means covering at least the entire periphery of the active agent carrier, the first adhesive means having a first coefficient of adhesion and the second adhesive means having a second coefficient of adhesion, the first coefficient of adhesion of the carrier layer to the active agent carrier being less than the second coefficient of adhesion of the active agent carrier to the skin, whereby upon application of the active agent carrier to the skin of the patient with the second adhesive means therebetween, the active agent carrier adheres to the skin of the patient and can be removed from the carrier layer thereby.

In accordance with this embodiment of the device of the present invention, the active agent carrier preferably comprises a reservoir containing the active agent, release means for the controlled release of the active agent from the reservoir, and an active agent impermeable barrier layer between the reservoir and the carrier layer whereby the active agent may only be released from the inner surface of the reservoir towards the skin or mucosa upon application of the active agent carrier to the skin or mucosa of the patient. In one embodiment thereof, the release layer comprises an active agent permeable membrane layer formed on the inner surface of the reservoir, whereby the reservoir is completely enclosed between the active agent permeable membrane layer and the active agent impermeable barrier layer.

In accordance with another embodiment of the present invention, a device has been provided for applying an active agent carrier to the skin or mucosa of a patient comprising a liner layer including a first surface and a second surface, the first surface comprising a releasable surface, a carrier layer for the active agent carrier, the carrier layer including a first surface and a second surface, hinge means permanently affixing the first surface of the liner layer to the first surface of the carrier layer at a predetermined location thereon, the active agent carrier being located on the first surface of the carrier layer at a location displaced from the hinge means, first adhesive means interposed between the first surface of the carrier layer and the active agent carrier for maintaining the active agent carrier in contact with the carrier layer when the portion of the carrier layer other than the hinge means is separated from the liner layer, and second adhesive means interposed between the first surface of the liner layer and the first surface of the carrier layer including the active agent carrier, for releasably maintaining the first surface of the carrier layer including the active agent carrier in contact with the first surface of the liner layer, the second adhesive means covering at least the entire periphery of the active agent carrier, the first adhesive means having a first coefficient of adhesion and the second adhesive means having a second coefficient of adhesion, the first coefficient of adhesion of the carrier layer to the active agent carrier being less than the second coefficient of adhesion of the active agent carrier to the skin, whereby upon application of the active agent carrier to the skin of the patient with the second adhesive means therebetween, the active agent carrier adheres to the skin of the patient and can be removed from the carrier layer thereby.

In accordance with this embodiment of the device of the present invention, the active agent carrier preferably comprises a reservoir containing the active agent, release means for the controlled release of the active agent from the reservoir, and an active agent impermeable barrier layer between the reservoir and the carrier layer whereby the active agent may only be released from the inner surface of the reservoir towards the skin or mucosa upon application of the active agent carrier to the skin or mucosa of the patient. In one embodiment thereof, the release layer comprises an active agent permeable membrane layer formed on the inner surface of the reservoir, whereby the reservoir is completely enclosed between the active agent permeable membrane layer and the active agent impermeable barrier layer.

In accordance with another embodiment of the present invention, a device has been provided for applying a film layer and an active agent carrier to the skin or mucosa of a patient comprising a liner layer including a first surface and a second surface, the first surface comprising a releasable surface, a carrier layer for the film layer and the active agent carrier, the carrier layer including a first surface and a second surface, hinge means permanently affixing the first surface of the liner layer to the first surface of the carrier layer at a predetermined location thereon, the film layer including a first surface and a second surface, the first surface of the film layer being located on the first surface of the carrier layer at a location displaced from the hinge means, a first adhesive layer interposed between the first surface of the carrier layer and the film layer for maintaining the film layer in contact with the carrier layer when the portion of the carrier layer other than the hinge means is separated from the liner layer, the active agent carrier being located on the second surface of the film layer, and a second adhesive layer interposed between the first surface of the liner layer and the first surface of the carrier layer including the film layer and the active agent carrier, for releasably maintaining the first surface of the carrier layer including the film layer and the active agent carrier in contact with the first surface of the liner layer, the second adhesive layer covering at least the entire periphery of the film layer, the first adhesive layer having a first coefficient of adhesion and the second adhesive layer having a second coefficient of adhesion, the first coefficient of adhesion of the carrier layer to the film layer being less than the second coefficient of adhesion of the film layer to the skin, whereby upon application of the film layer and the active agent carrier to the skin of the patient with the second adhesive layer therebetween, the film layer and the active agent carrier adhere to the skin of the patient, and the film layer and the active agent carrier can be simultaneously removed from the carrier layer.

In accordance with this embodiment of the device of the present invention, the active agent carrier preferably comprises a reservoir containing the active agent, release means for the controlled release of the active agent from the reservoir, and an active agent impermeable barrier layer between the reservoir and the film layer whereby the active agent may only be released from the inner surface of the reservoir towards the skin or mucosa upon application of the film layer and the active agent carrier to the skin or mucosa of the patient. In one embodiment thereof, the release layer comprises an active agent permeable membrane layer formed on the inner surface of the reservoir, whereby the reservoir is completely enclosed between the active agent permeable membrane layer and the active agent impermeable barrier layer. In a preferred embodiment, the active agent impermeable barrier layer extends peripherally beyond the reservoir about the entire periphery thereof so as to create an extended peripheral area of said active agent impermeable layer, and in a highly preferred embodiment the second adhesive layer includes an active agent permeable adhesive portion and an active agent impermeable adhesive portion, the active agent permeable adhesive portion corresponding to the active agent permeable membrane layer and the active agent impermeable adhesive portion corresponding to at least the extended peripheral area of the active agent impermeable barrier layer.

In accordance with another embodiment of this device of the present invention, the release means comprises a plurality of microcapsules containing the active agent encapsulated by an active agent permeable membrane. In this embodiment the second adhesive layer preferably includes an active agent permeable adhesive portion corresponding to the inner surface of the reservoir, and preferably the active agent impermeable barrier layer extends peripherally beyond the reservoir about the entire periphery thereof so as to create an extended peripheral area of the active agent impermeable barrier layer.

In accordance with another embodiment of this device of the present invention, the active agent permeable membrane layer extends peripherally beyond the reservoir so as to provide at least a portion of overlapping peripheral surfaces between the peripheral portion of the active agent permeable membrane layer and the peripheral portion of the active agent impermeable barrier layer, and the overlapping peripheral portions are heat sealed together to create an active agent impermeable seal surrounding the reservoir so that the active agent impermeable adhesive layer is applied to the active agent impermeable seal.

In accordance with another embodiment of the device of the present invention, the device for applying a film layer to the skin or mucosa of a patient comprises a liner layer including a first surface and a second surface, the first surface comprising a releasable surface, a carrier layer for the film layer, the carrier layer including a first surface and a second surface, the liner layer and the film layer having corresponding outer peripheries, hinge means permanently affixing the first surface of the liner layer to the first surface of the carrier layer at a predetermined location comprising a portion of the corresponding outer peripheries thereof, the film layer being located on the first surface of the carrier layer at a location displaced from the hinge means, temporary closure means for temporarily sealing the first surface of the liner layer to the first surface of the carrier layer at the remaining portion of the corresponding outer peripheries thereof so as to provide a sealed container for the film layer therein, a first adhesive layer interposed between the first surface of the carrier layer and the film layer for maintaining the film layer in contact with the carrier layer when the temporary closure means is unsealed and the portion of the carrier layer other than the hinge means is separated from the liner layer, and a second adhesive layer interposed between the first surface of the liner layer and the first surface of the carrier layer including the film layer for releasably maintaining the first surface of the carrier layer including the film layer in contact with the first surface of the liner layer, the second adhesive layer covering at least the entire periphery of the film layer, the first adhesive layer having a first coefficient of adhesion and the second adhesive layer having a second coefficient of adhesion, the first coefficient of adhesion of the carrier layer to the film layer being less than the second coefficient of adhesion of the film layer to the skin or mucosa of the patient, whereby upon application of the film layer to the skin or mucosa of the patient with the second adhesive layer therebetween, the film layer adheres to the skin or mucosa of the patient and the film layer can simultaneously be removed from the carrier layer.

In a preferred embodiment of this device of the present invention, the temporary closure means comprises a peelable heat seal formed between the first surface of the liner layer and the first surface of the carrier layer. In a preferred embodiment, the first surface of the liner layer comprises a first polymer layer, the first surface of the carrier layer comprises a second polymer layer, and the first and second polymer layers comprise different polymers whereby the peelable heat seal is formed therebetween. In accordance with another embodiment, however, in which the releasable surface comprises a siliconized coating, it is preferred that the first and second polymer layers comprise the same polymer.

In accordance with another embodiment of this device of the present invention, the first surface of the liner layer comprises a first polymer layer, the second surface of the liner layer comprises a paper layer, and the liner layer includes an intermediate layer between the first and second surfaces comprising a metallized film layer. Preferably, the first surface of the carrier layer comprises a first polymer layer, the second surface of the carrier layer comprises a paper layer, and the carrier layer also includes an intermediate layer between the first and second surfaces comprising a metallized film layer. In accordance with this embodiment, it is also highly preferable that the temporary closure means comprise a peelable heat seal formed between the first surface of the liner layer and the first surface of the carrier layer. Preferably, the liner layer and the carrier layer each has a substantially square configuration, so that the predetermined location for the hinge means comprises a first side of that square and the temporary closure means is located at the second, third and fourth sides of the square.

In accordance with another embodiment of the device of the present invention, the device for applying a film layer and an active agent carrier to the skin or mucosa of a patent comprises a liner layer including a first surface and a second surface, the first surface comprising a releasable surface, a carrier layer for the film layer and the active agent carrier, the carrier layer including a first surface and a second surface, the liner layer and the film layer having corresponding outer peripheries, hinge means permanently affixing the first surface of the liner layer to the first surface of the carrier layer at a predetermined location comprising a portion of the corresponding outer peripheries thereof, the film layer including a first surface and a second surface, the first surface of the film layer being located on the first surface of the carrier layer at a location displaced from the hinge means, temporary closure means for temporarily sealing the first surface of the liner layer to the first surface of the carrier layer at the remaining portion of the corresponding outer peripheries thereof, so as to provide a sealed container for the film layer and the active agent carrier therein, a first adhesive layer interposed between the first surface of the carrier layer and the film layer for maintaining the film layer in contact with the carrier layer when the temporary closure means is unsealed and the portion of the carrier layer other than the hinge means is separated from the liner layer, and a second adhesive layer interposed between the first surface of the liner layer and the first surface of the carrier layer including the film layer and the active agent carrier for releasably maintaining the first surface of the carrier layer including the film layer and the active agent carrier in contact with the first surface of the liner layer, the second adhesive layer covering at least the entire periphery of the film layer, the first adhesive layer having a first coefficient of adhesion and the second adhesive layer having a second coefficient of adhesion, the first coefficient of adhesion of the carrier layer to the film layer being less than the second coefficient of adhesion of the film layer to the skin or mucosa of the patient, whereby upon application of the film layer and the active agent carrier to the skin or mucosa of the patient with the second adhesive layer therebetween, the film layer and the active agent carrier adhere to the skin or mucosa of the patient and the film layer and the active agent carrier can simultaneously be removed from the carrier layer.

In a preferred embodiment of this device of the present invention, the active agent carrier comprises a reservoir containing the active agent, release means for the controlled release of the active agent from the reservoir, and an active agent impermeable barrier layer between the reservoir and the film layer, whereby the active agent may only be released from the inner surface of the reservoir towards the skin or mucosa of the patient upon application of the film layer and the active agent carrier to the skin or mucosa of the patient. Preferably, the release means comprises an active agent permeable membrane layer formed on the inner surface of the reservoir, whereby the reservoir is completely enclosed between the active agent permeable membrane layer and the active agent impermeable barrier layer. In a preferred embodiment, the active agent impermeable barrier layer extends peripherally beyond the reservoir about the entire periphery thereof so as to create an extended peripheral area of the active agent permeable barrier layer. In a highly preferred embodiment, the second adhesive layer includes an active agent permeable adhesive portion and an active agent impermeable adhesive portion, the active agent permeable adhesive portion corresponding to the active agent permeable membrane layer and the active agent impermeable adhesive portion corresponding to at least the extended peripheral area of the active agent impermeable barrier layer.

BRIEF DESCRIPTION OF THE DRAWINGS

FIG. 9 is a side, elevational, sectional view of a device for applying a film layer and an active agent carrier in accordance with the present invention;

FIG. 10 is a side, elevational, sectional view of the device shown in FIG. 9, with the film layer and active agent carrier applied in accordance with the present invention; and FIG. 11 is a side, elevational, sectional view of the film layer and active agent carrier of the device shown in FIG. 9 applied to the skin after removal of the carrier layer therefrom;

FIG. 12 is a side, elevational, sectional view of a device for applying an active agent carrier in accordance with the present invention;

FIG. 13 is a side, elevational, sectional view of the device shown in FIG. 12, with the active agent carrier applied in accordance with the present invention;

FIG. 14 is a side, elevational, sectional view of the device shown in FIG. 12 applied to the skin after removal of the carrier layer therefrom;

FIG. 17 is a side, elevational, sectional view of the device shown in FIG. 15;

FIG. 18 is a side, elevational, sectional view of the device shown in FIG. 17, with the film layer and active agent carrier applied in accordance with the present invention;

FIG. 19 is a side, elevational, sectional view of the device shown in FIG. 17 applied to the skin after removal of the carrier layer therefrom;

FIG. 20 is a partial, side, elevational, sectional view of another embodiment of the device of the present invention;

DETAILED DESCRIPTION

Figure 1:
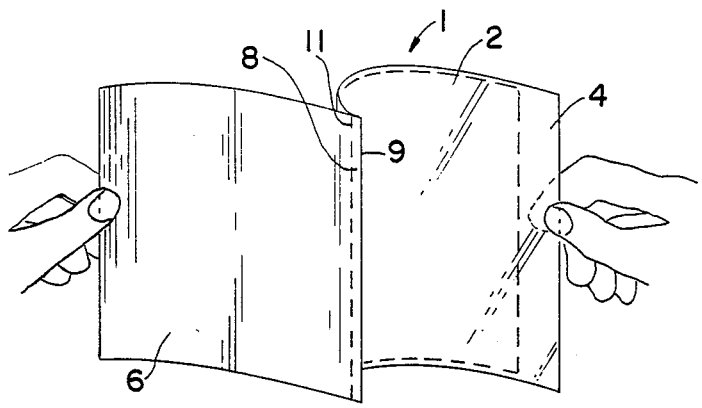
FIG. 1 is a top, elevational, perspective view of a device for applying a film layer in accordance with the present invention, after the initiation of the separation thereof.

The present invention can be more fully appreciated with reference to the above-noted figures and to the following detailed description thereof. In connection with the foregoing figures, like reference numerals will refer to like portions thereof.

Referring first to the embodiment of the present invention which is shown in FIGS. 1-4, this embodiment is intended to apply a film layer to the skin of a host. That is, the hinged applicator 1 of the invention includes a film layer 2, which can be most clearly seen in FIGS. 2-4, and which comprises an extremely thin and flimsy layer of material, which is preferably breathable and non-occlusive in nature. The film layer 2 is a material which would be extremely difficult, if not impossible, to handle by itself, i.e., apart from the hinged applicator 1 of the present invention. Film layer 2, which is shown after having been applied to the skin of the host in FIG. 4, in this embodiment is intended to act as a wound dressing. This film layer 2, or "skin," is thus a rather flimsy material, which preferably allows air and moisture vapor to pass therethrough, but which will not permit the passage of bacteria or other undesired elements or materials. It is preferred that film layer 2 thus be composed of various thin, plastic materials, or it can comprise an extremely thin foil layer, or layer of other non-woven materials, most particularly it will comprise a material which is sufficiently thin and flexible to be conformable to the skin, and will thus preferably be thinner than about 2 mils, preferably less than about 1.5 mils, and most preferably 1 mil or less.

These film layers 2 are preferably thermoplastic materials which are at least partially elastomeric in nature. They will therefore exhibit a high degree of elongation (preferably greater than about 130% elongation), and will thus exhibit excellent conformability characteristics without having the tendency to exhibit significant memory characteristics, although they will have some degree of recovery when stretched, for example. In terms of being breathable films it is preferred that these materials, in addition to permitting air to pass therethrough, will also permit moisture vapor to pass through them, at least more readily than is the case with materials such as polyethylene, for example. All of these film layers must be occlusive, at least with respect to particulates, in order to protect the wound, etc. However, their overall occlusive characteristics can then vary, depending upon the ultimate use intended for them in each particular case. In general, however, it is preferred that films be employed which are permeable to various glycols, such as polyethylene glycols, but rather occlusive films can also be employed in selected circumstances, including, for example, 1 and 2 mil layers of ethylene-vinyl acetate copolymers, or various nylon or polyester films. In addition, laminated or coated films could also be utilized, such as by employing a non-occlusive film such as those discussed above which is fully or partially selectively coated with an occlusive film.

The various thermoplastic films themselves can generally be produced with either a matte, glossy, or a clear surface, which is obtained by selection or modification of the surface of the chilling roller generally used downstream of the film extruder from which the film is extruded, and they can include various colors, such as skin color, as well as fillers, such as $TiO_2$, clay, or other such materials for the purpose of rendering the film opaque, and various organic additives, odor inhibitors, and/or various medications, etc. directly on the surface thereof.

From the commercial viewpoint, one of the most successful high moisture vapor permeable medical grade elastomeric films has been one of a series of products marketed by DuPont under the designation "Medifilm 800." These films are extruded from a class of elastomeric resins which are polyether block amides, commercially designated by the trademark PEBAX. The structure of these polymers can be generally represented by the formula:

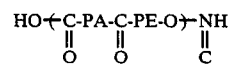

in which PA represents a relatively rigid polyamide segment and PE represents a relatively soft polyether segment. In this manner the extruded film products have high strengths in terms of high tear and abrasion resistance and at the same time provide a high degree of comfort or conformability, as well as moisture vapor permeability. The physical properties of two typical medical grade PEBAX films having a thickness of 1 mil are set forth in TABLE 1 herein.

TABLE 1

| PROPERTIES | FILMS | |
|---|---|---|
| | MEDIFILM 810 | MEDIFILM 827 |
| Tensile strength - psi (ASTM D882) | 3120 | 2200 |
| % Elongation | 430 | 800 |
| Modulus @ 50% elongation | 1600 | 900 |
| Initial tear resistance - lbs. (ASTM D-1004) | 0.65 | 0.6 |
| MUTR -g/m2/24 hrs. (ASTM E-96) 37.8 C/90% R.H. | 1675 | 2200 |

In addition, other such film layers 2 can comprise thermoplastic polyurethanes which also meet the above requirements. These include such commercial polyurethane compositions as Dow Chemical Company's PELLETHANE, including its 2363-80AE grade thereof; K. J. Quinn's Q-THANE; B. F. Goodrich's ESTANE; Mobay Chemical Company's TXIN; and others. Furthermore, these film layers 2 can also comprise various polyesters, such as the copolymers of various cyclic polyesters including DuPont's HYTREL, including its 4056 grade thereof, and General Electric's LOMOD, both of which are copolymers of polyether prepolymers and polybutylene terephthalate and polyisobutyl terephthalate, respectively, as well as Eastman Chemical's PCCE.

Figure 7:
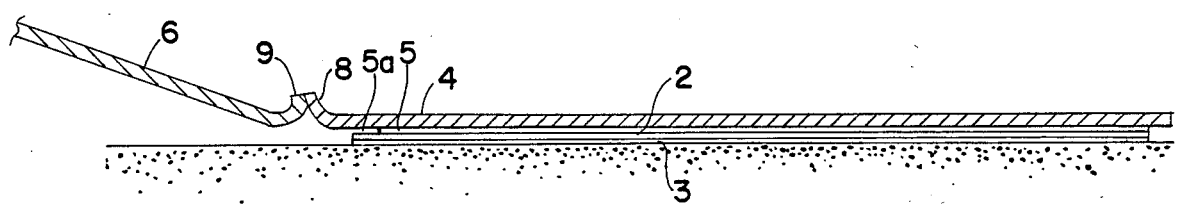
FIG. 7 is a side, elevational, sectional view of the device shown in FIG. 5, with the film layer applied to the skin.
Figure 8:
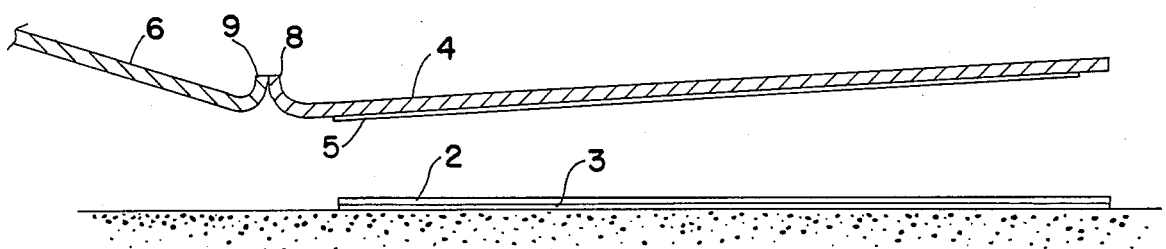
FIG. 8 is a side, elevational, sectional view of the device shown in FIG. 5, with the film layer applied to the skin and the carrier layer removed therefrom.

In order to adequately maintain the film layer 2 on the surface of the skin of the host, the only additional element required is a layer of adhesive 3 on the underside of film layer 2 as can best be seen in FIGS. 7 and 8.

As for the properties and characteristics of the adhesive to be used in this embodiment of the invention, it is primarily only necessary that the coefficient of adhesion thereof as between the film layer 2 and the skin surface to which it is being applied be sufficient to overcome the adhesive or other force holding the film layer 2 onto the hinged applicator 1 hereof, or more particularly to the carrier layer 4 to which the film layer 2 is adhered, as is discussed more fully below. Since the film layer 2 is preferably being applied to the skin, it should therefore be hypoallergenic. However, when this device is used in connection with the application of various drug delivery systems it will then have other more stringent requirements, such as most importantly its compatibility with the drug or drugs in question, as well as its resistance to alcohol or other solvents utilized therein, etc., all of which is discussed more fully below in connection with those embodiments of the invention. In connection with the application of film layer 2 above, however, an acrylic copolymer adhesive such as Avery Chemical Company's AS-351 HSX can be utilized, preferably at a coating weight of between about 25 and 35 g/m2. This pressure sensitive adhesive is a cross-linkable polymer which dries to provide a permanently tacky film having a total solids content of about 52%, a Brookfield viscosity (LVT/04/12 RPM @ 25° C.) of from about 15,000 to 25,000 cps and a weight per gallon of about 7.4 lbs. It can also be diluted with hexane or toluene to a desired solids and/or viscosity range, particularly for use in conventional coating equipment. Again, other such adhesives which are particularly useful together with drug delivery systems are discussed more fully below.

Referring again to FIGS. 1–4, the overall device 1 for carrying and applying film layer 2 to the skin of the host is shown therein. Thus, in its initial configuration the device includes a carrier layer 4 to whose underside is initially but temporarily affixed film layer 2. The film layer 2 can be affixed to the bottom surface of carrier layer 4 by means of another adhesive layer 5, but it can generally also be applied by means of any other means of temporarily adhering the film layer 2 to the carrier layer 4. This can therefore include means for heat sealing the film layer 2 to the carrier layer 4, or other such means for temporary lamination thereof.

Figure 5:
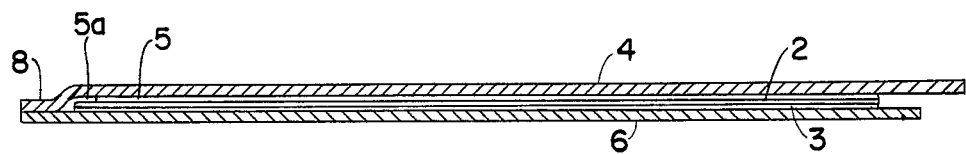
FIG. 5 is a side, elevational, sectional view of a device for applying a film layer in accordance with the present invention.
Figure 6:
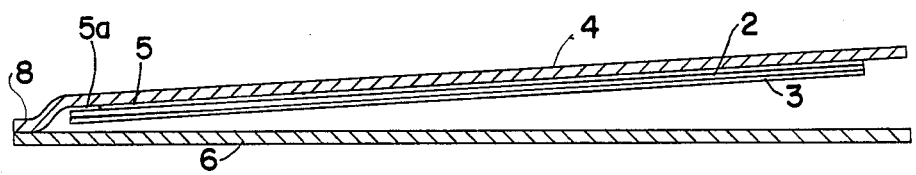
FIG. 6 is a side, elevational, sectional view of the device shown in FIG. 5 partially opened.

On an overall basis, the essential requirement here is to adhere the film layer 2 to the carrier layer 4 with sufficient strength to maintain it thereon when the film layer 2 is exposed, or uncovered by opening the liner layer 6 (see discussion below), while at the same time this bond is sufficiently weak in relative terms so as to readily peel off or be removable from the carrier layer 4 after the film layer 2 has been applied to the skin by means of the adhesive layer 3 discussed above. Within these parameters the film layer 2 can be adhered to the carrier layer 4 by means of an adhesive layer 5, which can be a pressure sensitive adhesive, such as a cross-linkable acrylic copolymer, etc., or by means of a heat sealable adhesive. It is important, however, to insure that the film layer 2 is readily removable from the inner surface of the carrier layer 4. This can be accomplished by leaving a narrow, predetermined area 5a (see FIGS. 5–7) which is free of such adhesive. Doing so prevents the film layer 2 from remaining affixed to the carrier layer 4 after the film layer 2 has been applied to the skin, as in FIG. 7, and the carrier layer 4 is pulled away from that surface. This requirement applies equally to those situations where other means, such as heat seals, etc., are used to affix the film layer 2 to the carrier layer 4, i.e.—it is still important to leave a small initial area of the film layer free of any adhesive means to facilitate removal thereof. Where the adhesive is an acrylic copolymer it can, for example, be essentially the same acrylic copolymer as that which is the adhesive layer 3 for applying the film layer 2 to the skin surface, including the materials such as the Avery Chemical Company AS-351 HSX adhesive, discussed above. Other such adhesives which can also be used for these purposes include an acrylic pressure-sensitive adhesive sold by National Adhesives under the designation DURO-TAK 80-1054. This adhesive has a solids content of 47.5%, a viscosity of 3,000 cps, and a plasticity (Williams) of 2.9 mm. It is generally used with a solvent system including ethyl acetate, heptane, isopropyl alcohol and toluene. Another such adhesive is sold by Monsanto under the designation GELVA Multipolymer Emulsion 2484, and comprises a stable aqueous acrylic emulsion pressure-sensitive adhesive having a solids content of 59%, and a viscosity of 1,500-Z, 300 cps. With these various adhesives the adhesion of this layer can be reduced as compared to adhesive layer 3 by the addition of a greater amount of cross-linking additives thereto and/or by utilizing different coating weights and/or viscosities therefor. In the case where carrier layer 4 is a paper layer, the plastic film layer 2 can be adhered thereto by coating its surface with a heat sealable adhesive and then heat sealing these two layers together. Alternatively, the film layer 2 and carrier layer 4 can be laminated together, such as where they are both plastic layers, or where they are different layers such as plastic film layer 2 and a paper carrier layer 4, by flowing the plastic film layer 2 onto the surface of the paper carrier layer 4—i.e., as an extrusion laminate.

Finally, the applicator device 1 of FIGS. 1–8 includes a liner layer 6 which is also initially but temporarily affixed to the underside of the carrier layer 4, as well as to the underside 3 of the film layer 2. Thus, in the laminate comprising this device in its initial state prior to use, the film layer 2 is sandwiched between the carrier layer 4 and the liner layer 6.

This liner layer 6 is itself intended to protect the film layer 2 prior to use and render it transportable while not interfering with its ultimate application. It can therefore comprise various layers, including paper or paper-containing layers or laminates; various thermoplastics, such as extruded polyolefins, such as polyethylene; foil liners; or various laminates of these different layers. However, this liner layer 6 must have an inner surface which is releasable with respect to the materials or layers with which it is initially in contact. It should therefore include a release coating, such as where a paper layer or the like is employed. This can be done in a conventional manner, such as by including a silicone or teflon coating on the surface thereof.

An element of the present invention which is particularly significant in terms of permitting one to utilize this device for its intended purpose of transferring film layer 2 from the device itself ultimately to the skin of the host in the required manner, is the presence of a relatively permanent hinge between the carrier layer 4 and the liner layer 6. In this case the hinge 8 between these two layers is effected along one edge 9 of the corresponding carrier and film layers which has an overall square configuration in connection with the particular device shown in FIG. 1. In this case the hinge comprises a permanent bond between these two layers, which can be effected in a number of ways, and which is discussed in more detail below.

The carrier layer 4 should be composed of a material which is also flexible, but which has considerably more substance and strength than does film layer 2. It should, however, be flexible enough to generally follow the contour of the area of the host where the film layer 2 is to be applied. On the other hand, it should have enough strength and substance so as to serve its function of carrying film layer 2 without wrinkling, etc. The actual material from which the carrier layer 4 can be produced can therefore include a variety of different materials. Some suitable materials for this layer include, for example, polyethylene, polypropylene, polyvinylidene chloride, polyethylene terephthalate, polyesters, polyamides, and others, as well as laminates of two or more of these layers with each other or with additional layers, such as foil, paper, various fabrics, etc., but in these cases preferably with the polymer layer on the inside, i.e.—in contact with and thereby carrying the film layer 2.

As for the liner layer 6, it is the purpose of this layer to enclose the film layer 1, and at the same time be easily removable therefrom, the initiation of which is shown in FIG. 1. Doing so thus exposes the underside of film layer 1 with adhesive layer 3 thereon for subsequent application to the skin of the host. It is thus preferable that the liner layer 6 include a release layer to permit its easy removal from the laminate composite of this device. The liner layer 6 can thus be composed of some of the same materials which are also suitable for use as the carrier layer 4 discussed above. This material, however, is made removable or releasable from the adhesive layers by, for example, treatment with silicone or other suitable coatings As an example, a preferred liner layer 6 will thus comprise a silicone or teflon release-coated paper, but it can also comprise various polyester films; foil layers, preferably coated with a polymer such as polyethylene; other such layers, including fabric layers, coated or laminated to various polymers, as well as extruded polyethylene, polyethylene terephthalate, various polyamides, and the like. The selection of a particular liner layer 6 will also depend upon other ultimate requirements of the particular device in question, including whether there is a desire for a transparent or opaque liner, etc. It can thus be seen that essentially throughout the area of contact between the carrier layer 4 and the liner layer 6, although there is adhesive present on at least a portion of the underside of the carrier layer 4 in contact with the liner layer 6 to maintain these two layers in contact, and preferably at least the entire periphery thereof, that the seal throughout that area is "peelable," or releasable, by merely pulling apart the edge of the liner layer 6, again as is shown in FIG. 1. At the same time, when this is done the film layer 2 remains in contact with the lower surface of the carrier layer 4 because of the above described relationship between the adhesive materials in the adhesive layer 5 maintaining the film layer 2 in contact with the carrier layer 4 vis-a-vis the adhesive layer 3 between the lower surface of the film layer 2 and/or carrier layer 4 and the liner layer 6.

Furthermore, in order to facilitate initiation of the separation of the carrier layer 4 from the liner layer 6, the corresponding edge portions thereof can be free of adhesive (see right-hand side of FIGS. 5 and 6) so as to act as a starting tab or portion thereof which are effectively already separated from each other. Other such means can, however, also be employed for this purpose. For example, one of the carrier layer 4 or liner layer 6 could extend beyond the other such layer, to facilitate grasping of same, or a slit can be provided in one of these layers to permit peeling back of the leading edge thereof. Other such methods will be apparent to those of ordinary skill in this art.

In view of the above, it will become apparent that in the case where the releasability discussed above is effected throughout the entire area of contact between the carrier layer 4 and the liner layer 6, the two layers will be completely separable. This, however, renders use of the device of this invention far more difficult, as is more fully discussed below. Therefore, a highly preferred embodiment of this invention employs hinge 8 between these two layers so as to create a permanent bond therebetween. In this case, this can be accomplished by providing an area which is delineated by imaginary line 11 in FIG. 1 and within which hinge 8 is provided. In this example, this is accomplished by providing that within the area of imaginary line 11 corresponding to the liner layer 6, that portion of the liner layer 6 corresponding thereto does not include the siliconized layer or other coating which renders the paper liner layer 6 releasable throughout the remainder of this area. In this manner, at the location delineated by imaginary line 11 there is direct contact between the material comprising the liner layer 6 and the material comprising the carrier layer 4, again with no siliconized or release coating therebetween. Thus, within this area it is possible to create a permanent bond, and this can be readily accomplished in this case by application of the very same adhesive which is used throughout the remainder of the area of contact between the carrier layer 4 and the liner layer 6. However, in the area without the intervening presence of the siliconized or other release coating, a permanent bond is established, or, in other words, is not interrupted by the presence of a release coating or the like. It will also be understood that the term "permanent bond" is a relative term, at least to the extent that this bond must be more "permanent" than the releasable bond between the liner layer and the carrier layer throughout the remaining portions thereof.

The above discussion represents only one way in which a permanent bond can be created between the carrier layer 4 and the liner layer 6. Such a bond can also be created in a variety of other ways. For example, the hinge 8 can be produced by creating a heat seal between the carrier layer 4 and the liner layer 6. In that case, it would generally be required that compatible thermoplastic material be in contact at the hinge area 8 in order to provide such a heat seal. For example, where the carrier layer is polyethylene film, and the liner layer 6 is polyethylene film laminated onto a carrier such as paper or the like, the pair of contacting polyethylene layers can be readily heat sealed together to form hinge 8. In addition, a heat sealable coating, such as a layer of polyvinylchloride or polyvinylidene chloride (SARAN) can be applied to the surface of one of these layers, and the two layers then bonded by heat without the need for excessive pressure therebetween in order to do so. Another possible means of creating the hinge 8 would be to leave the release coating, such as a silicone or teflon layer, on a liner layer 6, such as a paper layer, and then over this release coating apply an adhesive strip or some other means to permanently bond the liner layer 6 to the carrier layer 4. Furthermore, the hinge 8 can also be provided by other mechanical means, including staples, mechanical crimping, or the like.

Figure 2:
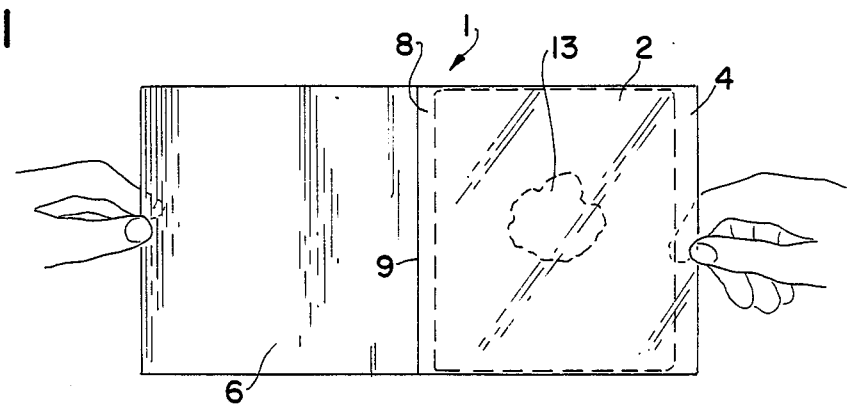
FIG. 2 is a top, elevational, perspective view of the device of FIG. 1, fully opened.

As can also be seen in FIGS. 1 and 2, it is critical to the device of the present invention that, in those embodiments in which a hinge 8 is employed, the edge of the film layer 2 which is adjacent to imaginary line 11 and which defines hinge 8 be displaced from the hinge 8 by a distance which is at least sufficient to permit removal of the film layer 1 without interference from hinge 8. Quite clearly, if the film layer 2 extends to within the hinge area 8, it will be firmly affixed between the hinge elements, and it will therefore become difficult, if not impossible, to remove the film layer 2 from the carrier layer 4. Also, while the siliconized portion of liner layer 6 may, in the embodiment discussed above, terminate at or near imaginary line 11 defining hinge 8, at the same time it must extend beyond the area corresponding to the end of film layer 2 which is adjacent to the imaginary line 11, again in order to insure that the carrier layer 4 and the liner layer 6 are peelably separable at that location, and that film layer 2 can thus be removable therefrom.

Turning to FIG. 2, after the liner layer 6 has been peeled completely away from the carrier layer 4, except for the hinge area 8, and the device has been completely opened into the configuration which is shown in FIG. 2, the combination of carrier layer 4 and film layer 2 can then be applied to the skin of the host at the location of a wound 13. Again, because of the required flexibility of carrier layer 4, it is then a relatively easy matter to apply pressure to the upper side of carrier layer 4 against the skin so as to firmly adhere film layer 2 and carrier layer 4 to the area of the skin surrounding the wound 13. The adhesive 3 which is present on the underside of film layer 2 will thus firmly affix the film layer 2 to that area of skin completely surrounding the wound 13.

Figure 3:
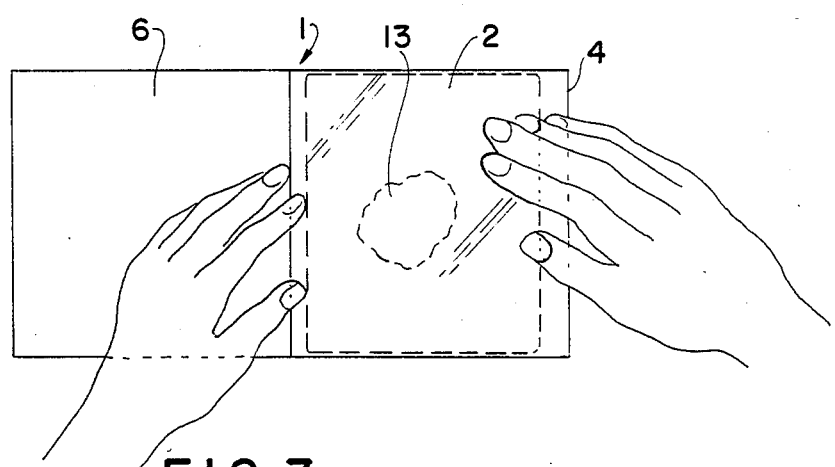
FIG. 3 is a top, elevational, perspective view of the device of FIG. 1, with the film layer applied to the skin.
Figure 4:
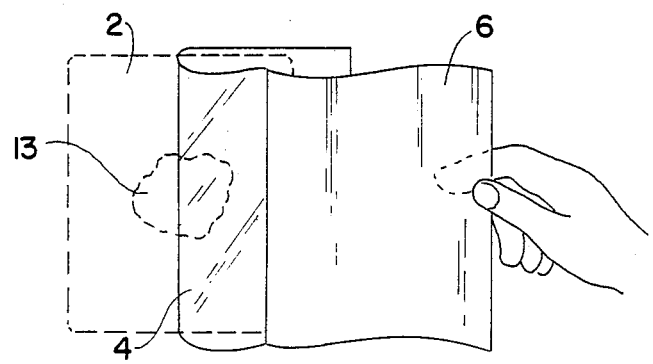
FIG. 4 is top, elevational, partial perspective view of the film layer of the device shown in FIG. 1 applied to the skin along with a portion of the carrier layer removed therefrom.

The next step in application of this device involves removal of the cover layer 4. This can now be easily accomplished by merely pulling the liner layer 6, which therefore now acts as a tab, and lifting same. Because the coefficient of adhesion of the film layer 2 to the skin of the host is now greater than the coefficient of adhesion of the adhesive which is present between the film layer 2 and the carrier layer 4, lifting of the liner layer 6 easily removes the carrier layer 4 from the film layer 2 without removing the film layer 2 from the skin of the host. This procedure can be further facilitated by the above-described procedure of having the leading edge of the film layer 2 free of the adhesive layer 5 which is holding the film layer 2 to the surface of the carrier layer 4, so as to leave area 5a free of such adhesive layer 5. Thus, upon initiation of the removal of carrier layer 4 (see FIG. 4) the leading edge readily separates from the carrier layer 4, since they are not attached by adhesive at that location. On the other hand, the film layer 2 at that end point readily adheres to the skin, since it does include a portion of the adhesive layer 3 on its underside. Further pulling against the end of liner layer 6 thus readily removes the remainder of the carrier layer 4 from the film layer 2 since a portion of the film layer is already adhesively secured to the skin of the host. The entire cover layer 4, which remains attached to the liner layer 6 by means of hinge 8, is then easily removed from the surface of the film layer 2, and as shown in FIG. 3, thus leaving the film layer 2 properly affixed to the skin of the host, covering the wound 13 in a relatively flat and undisturbed configuration, while the remainder of the device including cover layer 4, has been completely removed and can then be discarded. it has thus been possible to apply the extremely thin and flimsy film layer 2 to the skin as required, in a manner which would have been impossible without the device of this invention.

The present invention can also be utilized to transfer an active agent carrier to the skin or mucosa of a patient or host either alone, or in a preferred embodiment, along with film layer 2. In these embodiments of this invention, the active agent carrier itself can be applied from the carrier layer 4, much as the film layer 2 is applied in the devices discussed above, or where both the active agent carrier and film layer 2 are applied to the host, the film layer 2 in effect operates as a carrier for the active agent carrier itself, so that both are simultaneously applied to the skin in accordance with the general procedure discussed above in connection with FIGS. 1–4. As can be seen in FIGS. 9–11, the active agent carrier 15 is affixed to the underside of film layer 2a so that ultimately both film layer 2a and active agent carrier 15 will be applied to the skin 16 of the host. As can be seen in FIGS. 12–14, the active agent carrier 15a itself can be applied to the skin 16a of the host.

Referring specifically to the active agent carrier 15 as shown in FIGS. 9–14, the active agent is contained in a separate and distinct reservoir 17 created by a backing member 19 and a membrane 21 sealed to each other about the circumference or perimeter of the membrane, preferably by means of a heat seal. An active agent permeable adhesive layer 23 can be applied to the surface of the membrane opposite the reservoir 17. That is, reference can be made to the above discussion with respect to the adhesive layer 3 in the embodiment of FIGS. 1–4 which is interposed between the liner layer 6 and the bottom face of the film layer 2. In this case the portion of that adhesive layer which is at the location of the membrane 21 of the active agent carrier 15 must be an active agent permeable adhesive layer, i.e., so the active agent can permeate through that layer when it is eventually interposed between the active agent and the skin of the host into which it is intended to penetrate. However, the active agent permeable adhesive layer 23 should be limited to the area of the membrane 21 as shown in FIG. 9, and the remaining portion of the adhesive necessary for coating the surface of the liner layer 6a can comprise an active agent impermeable adhesive layer which is discussed in more detail below. The reason for this is that the use of an active agent permeable adhesive over the entire surface of the liner layer 6a, or at least beyond the periphery of the active agent carrier 15, would concomitantly increase the drug delivery surface, and the treatment dosage for the particular drug delivery system in question would be undesirably altered thereby. In addition, in the embodiment where a film layer 2a is being transferred along with the active agent carrier 15 (as in FIGS. 9-11), the remainder of the surface of the film layer 2a can include a layer of active agent impermeable adhesive 27, and more particularly a strong adhesive for maintaining the film layer 2a in firm contact with the skin of the host. In that case the presence of an adhesive layer on the surface of the active agent carrier becomes of little significance, since that surface will be maintained in contact with the skin by means of the surrounding adhesive layer 27 in contact with the film layer 2a. However, it is still preferable to employ an active agent permeable adhesive layer in contact with the active agent carrier, or at least for assuring the maintenance of contact between the active agent carrier and the skin of the host. For that purpose a contact type adhesive, of substantially less strength, can thus be utilized.

As for the outer surface of film layer 2 which is in contact with carrier layer 4a, the same discussion set forth above with respect to adhesive layer 5 employed in the embodiment of FIGS. 1-4 applies equally in this embodiment. It is therefore once again preferred to leave a "leading edge," such as area 5a in FIGS. 1-4, free of adhesive layer 5 to facilitate transfer of the film layer 2a, now along with active agent carrier 15, from the carrier layer 4a to the skin.

Returning to the active agent carrier 15, in the embodiment shown in FIGS. 9-11, in which a film layer 2a is employed, a layer 27 of an active agent impermeable adhesive is disposed on the inner surface of the film layer 2a. This adhesive thus affixes the film layer 2a to the outer backing member 19 of the active agent carrier 15, and also covers the periphery of the film layer 2a surrounding the active agent carrier 15. The active agent permeable adhesive layer 23 and the active agent impermeable adhesive layer 27 are thus positioned so that, when the liner layer 6a (e.g., a silicone-release-coated polyethylene terephthalate film) is removed, these two adhesive layers can be applied to the skin or mucosa. In this case the active agent impermeable adhesive layer 27 thus extends beyond the active agent carrier 15 and provides adhesive for the entire inner surface of the film layer 2a surrounding same.

The film layer 2a and the impermeable adhesive layer 27 thus form a pocket surrounding the backing member 19, the reservoir 17, the membrane 21 and the active agent permeable adhesive layer 23 so that, when the device is adhered to the skin or mucosa, the active agent can be released through the membrane 21 and through the active agent permeable adhesive layer 23 to provide a continuous dose of the active agent therethrough, but cannot permeate through the film layer 2a or radially outwardly through the active agent impermeable adhesive layer 27.

It is also possible to eliminate the backing member 19 so that the reservoir 17 in this case is created in the space between the active agent impermeable adhesive layer 27 and the membrane 21.

The outer surface member, that is the member of the active agent carrier which is in contact with the film layer 2a, be it a separate overlay covering layer or the backing member 19 described above, is preferably a thin film or sheet. In many instances, because of the area of skin to which the device is to be attached, the device is flesh colored for cosmetic reasons. Preferably, it is a clear polyester layer, which is occlusive with respect to the active agent or drug, but it can also be dyed various colors, or include printed matter thereon. The outer surface layer normally provides support and a protective covering for the device.

The outer surface layer is preferably made of a material or combination of materials which is substantially impermeable to the layer or layers with which it can be in contact, i.e., to the active agent, the impermeable and permeable adhesives, etc. However, a primary purpose is to prevent seepage of the active agent through the outer surface layer of the device so, if the outer surface layer is coated on the surface in contact with the remainder of the device with the active agent impermeable adhesive layer, this impermeable adhesive layer will perform this purpose even if the outer surface layer is not totally impermeable to the active agent. Thus, it is not necessary in all instances that the outer surface layer be impermeable to the active agent, although in most instances it normally is. By substantially impermeable we mean that the other components in contact with the layer or component under consideration will not appreciably permeate through such layer or component for the normal period of use and storage of the device, see the discussion of impermeability, infra.

The above discussion also applies to the embodiments shown in FIGS. 12-14, in which only the active agent carrier 15 is being applied to the skin, and no film layer 2a is thus included therein. In this embodiment the adhesive layer 27 between the carrier layer 4a and the outer surface of the active agent carrier 15, such as overlay covering layer 18, will comprise the same adhesives discussed above for holding the film layer 2 to the surface of the carrier layer 4 prior to application of the film layer 2 to the skin of the host, as is specifically set forth in the embodiment of FIGS. 1-4. It is noted in this regard that this adhesive layer is not specifically shown in FIGS. 12-14, as is corresponding layer 5, for example, in FIGS. 1-4. In this case it is intended to essentially coincide with carrier layer 4a, or at least the surface thereof in contact with the active agent carrier 15, again except for the preferred omission of the adhesive from a leading edge thereof.

In any event, the structure of the particular active agent carrier 15 shown in FIGS. 12-14, again includes an active agent contained in a reservoir 17 created by a backing member 19 and a membrane 21, which are again sealed to each other about the perimeter of the membrane. An active agent permeable adhesive layer 23 is again employed. Furthermore, in this embodiment an overlay covering layer 18 with a layer of the active agent impermeable adhesive 27 thereon is employed which has a sufficient surface area and shape such that, when attached to the backing member 19, they overlap same completely. In this manner, the active agent impermeable adhesive layer 27 surrounds at least the periphery of the active agent permeable adhesive layer. The overlay covering layer 18 and the impermeable adhesive layer 27 thus form a pocket surrounding the backing member 19, the reservoir 17, the membrane 21, and the active agent permeable adhesive layer 23 so that, when the device is adhered to the skin or mucosa, the active agent can be released through the membrane 21 and through the active agent permeable adhesive layer 23 to provide a continuous dose of the active agent therethrough, but cannot permeate through the outer surface layer 18 or radially outwardly through the active agent impermeable adhesive layer 37. It is also possible to eliminate the backing member 19, so that the reservoir 17 is then created in the space between the active agent impermeable adhesive layer 27 and the membrane 21 to which the active agent impermeable adhesive layer 27 is attached at the perimeter of the membrane 21. In yet another embodiment, the overlay covering layer 18 is not employed, but the backing member 19 is used and is impermeable to the active agent and thus performs the function of the outer surface layer. Various elements of these embodiments are also specifically disclosed in U.S. Pat. No. 4,573,996, which are incorporated herein by reference thereto.

The actual material used for the outer surface layer, i.e., the overlay covering layer 18 and/or the backing member 19, will depend on the properties of the materials in contact therewith. Some suitable materials for the outer surface layer include, for example, cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride, paper, cloth, and aluminum foil.

The material which forms the outer surface layer, either the overlay covering layer 18 or the backing member, may be flexible or non-flexible. Preferably, a flexible outer surface layer is employed to conform to the shape of the body member to which the device is attached.

Preferably, the material which forms the overall covering layer 18 and/or the backing member 19 is a film or a composite of films. The composite can be a metallized (e.g., aluminized) film or a laminate of two or more films or a combination thereof. For example, a laminate of polyethylene terephthalate and polyethylene or a polyethylene/metallized polyethylene terephthalate/polyethylene laminate can be employed. The preferred polymers include polyethylene, polypropylene, polyvinyl chloride and polyethylene terephthalate.

As mentioned above, a primary purpose of the active agent impermeable adhesive layer, such as layer 27 in the embodiment of FIGS. 9–11, is to provide adhesion to the skin or mucosa, to prevent seepage of the active agent from the device during storage and use, and to maintain the overall film layer against the skin or mucosa surrounding the active agent carrier. Thus, any adhesive which performs these functions will be suitable for use in the present invention. The degree of impermeability of the active agent impermeable adhesive layer to the active agent will vary depending upon the active agent, carrier, transportation agent, etc. Preferably, the active agent impermeable adhesive layer is a pressure sensitive adhesive suitable for contact with the skin or mucosa, e.g., dermatologically acceptable. Examples of suitable pressure sensitive adhesive for use in the present invention as the active agent impermeable adhesive layer include natural rubber adhesives such as R-1072 from B. F. Goodrich Co., No. 735 from C. L. Hathaway, and No. 5702 from EvansSt. Clair; acrylic adhesives such as PS-41 from C. L. Hathaway, Vr-0833 from H. B. Fuller, Adcote 73A207A from Morton Chemical, Nos. 80-2404, 80-1054, 72-9056, and 72-9399 from National Starch, Nos. E-2015, E-2067 and E-1960 from Rohm & Haas, M-6112 from Uniroyal Inc. and Daratak 74 L from W. R. Grace; and synthetic rubber adhesives such as Jowatherm 270-00 and Jowatherm S-3202 from Jowat Corp. and 70-9416 from National Starch.

The width and thickness of the impermeable adhesive layer for contact with the skin or mucosa is that width and thickness which provides at least sufficient impermeability to the active agent (and if necessary to the other components of the device with which the impermeable adhesive layer is in contact) so that the active agent does not seep out of the device as explained above. Some suitable widths include 1/16 to 2 inches, and preferably ⅛ to 1 inches. In most instances, the width will be ¼ to ½ inch depending on the specific use. The width and thickness need not be uniform and may vary around the perimeter of the device, e.g., to provide a specific geometric shape or to provide a tab for removal of a protective liner.

The active agent permeable adhesive layer also joins the device to the skin or mucosa of the host, but in the case where the active agent carrier is being applied along with the film layer 2a, as is discussed above, the active agent permeable adhesive layer is used primarily to maintain contact, and thus it can have less adhesive strength. Therefore, the adhesive is preferably dermatologically acceptable. The active agent permeable adhesive layer is also preferably a pressure-sensitive adhesive. Any of the well-known, dermatologically acceptable, pressure-sensitive adhesives which permit drug migration therethrough can be used in the present invention. Some suitable permeable adhesives include acrylic or methacrylic resins such as polymers of esters of acrylic or methacrylic acid (e.g., n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol esters thereof), alone or copolymerized with ethylenically unsaturated monomers such as acrylic acid, methacrylic acid, acrylamide, methacrylamides, N-alkoxymethyl acrylamides, N-alkoxymethyl methacrylamides, N-t-butylacrylamide, itaconic acid, vinyl acetate, N-branched alkyl maleamic acids wherein the alkyl group has 10 to 24 carbon atoms, glycol diacrylates, or mixture of these monomers; natural or synthetic rubbers such as silicon rubber, styrenebutadiene rubber, butyl-ether rubber, neoprene rubber, nitrile rubber, polyisobutylene, polybutadiene, and polyisoprene; polyurethane elastomers; vinyl polymers, such as polyvinyl alcohol, polyvinyl ethers, polyvinyl pyrrolidone, and polyvinyl acetate; urea formaldehyde resins; phenol formaldehyde resins; resorcinol formaldehyde resins; cellulose derivatives such as ethyl cellulose, methyl cellulose, nitrocellulose, cellulose acetate butyrate and carboxymethyl cellulose; and natural gums such as guar, acacia, pectina, starch, destria, gelatin, casein, etc. The adhesives may also be compounded with tackifers and stabilizers as is well-known in the art.

The permeable adhesive layer preferably contains some of the active agent when the device is placed on the skin. This provides an initial drug presence at the skin or mucosa and eliminates delay in absorption of the active agent or in topical application, if that is desired. Thus, the drug is immediately available to the host. The initial drug presence may be due to the permeations through the membrane and/or to an amount of the drug mixed in with active agent permeable adhesive layer during manufacture, while on the other hand a surrounding layer of active agent impermeable adhesive serves to limit and clearly define the area of drug administration.

The amount of the active agent present in the permeable adhesive layer depends on the initial drug presence desired, e.g., for a pulse dosage. For example, U.S. Pat. No. 4,031,894 discloses that 10–200 micrograms scopolamine base per $cm^2$ effective surface area is a suitable initial amount of active agent in the permeable adhesive layer.

The width and thickness of the permeable adhesive layer for contact with the skin or mucosa is that width and thickness which provides sufficient permeability to the active agent and a suitable surface area to allow the dosage rate desired to the skin or mucosa. These widths and thicknesses are conventional in the art and therefore need not be discussed in detail here.

In most instances, the impermeable adhesive layer will extend to the outer rim of the device. However, as pointed out above, the backing member or overlay covering layer may extend radially outwardly past the impermeable adhesive layer to provide a tab for removal of the protective liner from the remainder of the device for application of the device to the skin or mucosa. Also, the impermeable adhesive layer is in most instances in direct contact and/or adjacent to the permeable adhesive layer. However, this is not necessary and there may be a gap between the permeable adhesive layer and the impermeable adhesive layer if desired.

The thickness and shapes of the permeable and impermeable adhesive layers in the device of the present invention need not be the same or correspond. This is a particular advantage to the invention in that the device can be made to adhere to specific portions of the skin or mucosa by primary means of the impermeable adhesive layer while not affecting the surface area of the permeable adhesive layer through which the active agent passes (i.e., the shape of the device can be varied without varying the surface area of the membrane and permeable adhesive layer which determines the amount of active agent delivered to the skin or mucosa).

The reservoir is separated from the permeable adhesive layer by a membrane. The membrane may be microporous in which case the pores become filled with active agent from the reservoir. The membrane may also function in any other way as long as the active agent permeates through the membrane at a suitable rate. The membrane and the permeable adhesive layer can be monolithic. In this instance, the surface of the membrane is treated to make it adhesive in nature so that it will adhere to the skin or mucosa but still provide membrane permeability characteristics.

The suitability of the rate of permeation of the active agent through the membrane depends on the desired dosage rate and the permeability of the active agent through the skin or mucosa, if transdermal type administration is desired. An effective amount of the active agent is contained in the reservoir to provide the desired dosage. Sometimes, the skin or mucosa itself determines the rate at which the active agent will be administered therethrough. In these latter instances, if the dosage rate through the skin or mucosa is the dosage rate desired, the membrane need not provide any limiting rate of permeation function but need only supply sufficient active agent to the skin or mucosa to allow the desired permeation through the skin or mucosa which itself determines the dosage rate at which the active agent will be absorbed by the host.

The materials suitable for use as the membrane are conventional in the art and need not be discussed in detail here. Some preferred materials for a separate membrane layer may be, for example, polypropylene, polycarbonates, polyvinyl chloride, cellulose acetate, cellulose nitrate, and polyacrylonitrile. Some suitable encapsulating membrane materials include, for example, hydrophobic polymers such as polyvinyl chloride either unplasticized or plasticized with long-chain fatty amides or other plasticizers, plasticized nylon, unplasticized soft nylon, silicone rubber, polyethylene, and polyethylene terephthalate. Hydrophilic polymers can also be employed such as esters of acrylic and methacrylic acid (e.g., as described in U.S. Pat. Nos. 2,976,576 and 3,220,960 and Belgium Pat. No. 701,813); modified collagen; cross-linked hydrophilic polyether gels (e.g., as described in U.S. Pat. No. 3,419,006); cross-linked polyvinyl alcohol; cross-linked partially hydrolyzed polyvinyl acetate; cellulosics such as methyl cellulose, ethyl cellulose, and hydroxyethyl cellulose; and gums such as acacia, carboxymethylcellulose, and carageenan alone or combined with gelatin.

The active agents suitable for use in the present invention may be, for example, systemic or topical drugs. Individual active agents or mixtures thereof, if desired, can be employed. Any drug which passes through the skin or mucosa can be employed for internal administration in the device of the invention, so long as the drug will pass through the permeable adhesive layer and the material forming the membrane or microcapsules.

Suitable systemic drugs for administration by the claimed device include those useful in treating emesis and nausea as is described in U.S. Pat. No. 4,031,894, e.g., preferably, scopolamine.

Other suitable drugs include the coronary vasodilators described in U.S. Pat. No. 3,742,951 such as compounds having nitrate moiety. Some suitable coronary vasodilators as well as other suitable systemic drugs are disclosed in U.S. Pat. Nos. 3,996,934 and 4,573,996, and the portions of both of these describing same are incorporated herein by reference thereto.

Another embodiment of the device of the present invention which is also suitable for use in transferring both a film layer and an active agent carrier in accordance with the present invention is shown in FIGS. 15-19 hereof. In particular, and in connection with the manufacture and sale of various transdermal patches in the past, in many cases relatively volatile solvents such as ethanol are utilized in connection with the drugs employed therein. There has thus been a problem in connection with the need to maintain these patches in a sealed envelope or container so that these solvents do not prematurely evaporate, thus damaging the potency of the drug carried therein. These transdermal patches have thus been generally sealed into separate, tearable envelopes or the like in connection with their marketing. In a preferred embodiment of the present invention, however, the carrier and liner layers of the present invention can themselves act as such a container, thus greatly simplifying the overall commercial product and considerably reducing its cost, while in fact increasing its effectiveness. Most particularly, by sealing the outer periphery of these containers in a manner which is discussed in more detail below, this can be readily accomplished, while at the same time incorporating all of the other features set forth above in connection with the device for transferring the film and active agent carriers hereof.

Figure 15:
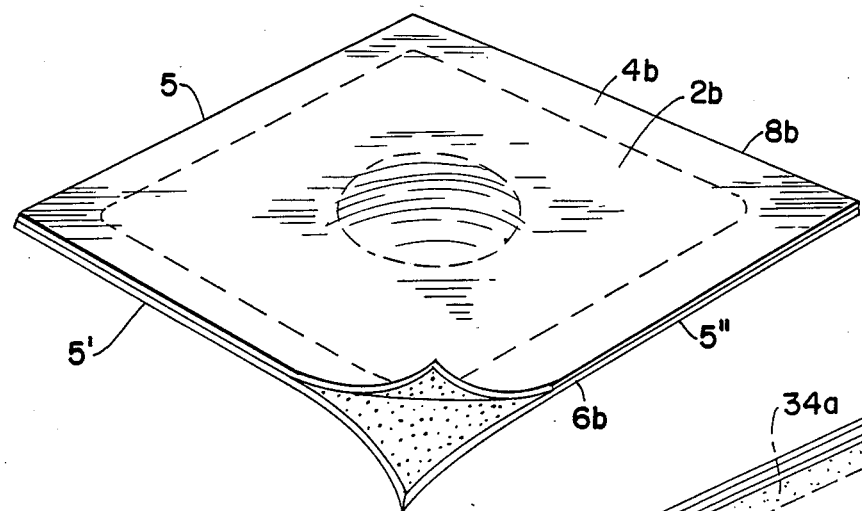
FIG. 15 is a top, elevational, perspective view of a sealed device for applying a film layer and an active agent carrier in accordance with the present invention.
Figure 16A:
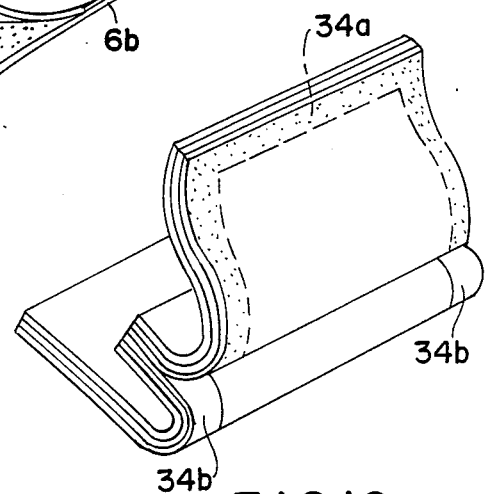
FIG. 16a is a top, elevational, perspective view of another embodiment of the carrier layer of FIG. 16 removed from the skin after application of the film layer and active agent carrier to the skin.
Figure 16:
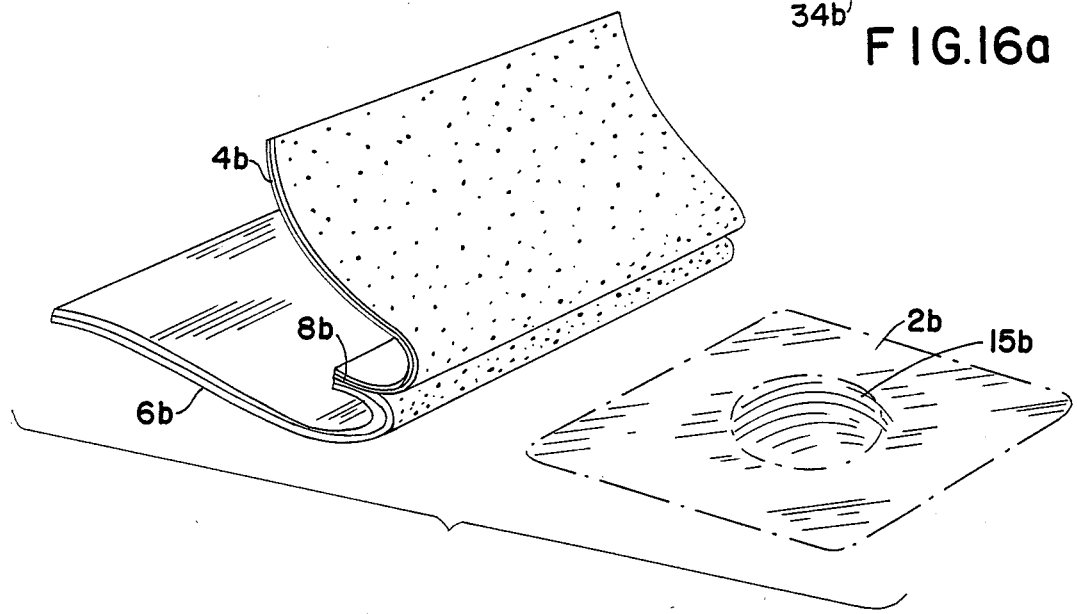
FIG. 16 is a top, elevational, perspective view of the film layer and active agent carrier of FIG. 15 applied to the skin, and with the carrier layer removed therefrom.

In accordance with this embodiment of the present invention, the hinge 8b corresponding to the hinges discussed above is a preferred element for use in the present invention, but is not absolutely essential in every embodiment thereof. Thus, in the embodiment shown in FIGS. 15 and 16 a relatively permanent hinge 8b is included in the device for the same purposes as is the case with hinges 8 and 8a above. However, in this case, at the other three sides of the square device which is shown in FIGS. 15 and 16 (and in this location also where such a permanent hinge is not utilized), a "peelable seal" is created between the carrier layer 4b and the liner layer 6b. In the embodiment shown in these Figures, both the carrier layer and the liner layers, 4b and 6b, respectively, comprise three-layered laminates, in this case preferably comprising outer layers of paper or the like, intermediate layers of aluminized foil or the like, and inner polymer layers, such as polyethylene and the like. However, a wide variety of layers and/or laminates can be employed in this embodiment, primarily requiring that they protect the product contained therewithin, and that they be sealable in nature.

The same is true with respect to the liner layer 6b, so that in this preferred embodiment the device is composed of two facing polyethylene inner layers. The creation of a "peelable seal" along the edges 5, 5' and 5" for this device is then accomplished in the manner disclosed in U.S. Pat. No. 4,710,191, the disclosure of which is incorporated herein by reference thereto. In particular, in that patent it is disclosed that such a "peelable seal" can be created by the incorporation of a release coating on the inner surface of a layer such as liner layer 6b so as to render the heat-sealed area then created between these two layers, in this case between liner layer 6b and carrier layer 4b, by weakening the thermal bond created therein. It is also disclosed in this patent that one alternative for achieving this result is to employ two different materials as the inner layers for the liner layer 6b and the carrier layer 4b, such as polyethylene and polypropylene. In such a case no release coating is then required on the inner surface of the liner layer 6b, at lease for the purposes of creating such a peelable seal at these locations around the remainder of the periphery thereof.

In another embodiment, however, such a peelable seal can be created in a different manner. Referring to FIGS. 16a and 20, it can thus be seen that between the two facing polyethylene layers 34 and 34a a permanent seal is created, such as by heat sealing or by the application of a direct adhesive bond therebetween. However, in order to render this seal peelable, a perpendicular slit 40 is then provided in layer 34a, so that the seal can now be broken by separation between the polyethylene layer 34a and its adjacent backing layer, or foil layer 32a, which is a far weaker bond created by the heat seal between these differing layers.

The result of this can be best seen in FIG. 16a, in which a U-shaped strip of the polyethylene layer 34a has been transferred to the inner face of the corresponding polyethylene layer 34 of the carrier layer 30, leaving only two layers, 30a and 32a, at the corresponding outer periphery of the liner layer 30a upon the separation of the carrier layer from the liner layer.

As for the remaining elements in the device shown in FIGS. 15-19, the film layer 2b is again incorporated onto the underface of the liner surface of carrier layer 4b in the same manner as is discussed above, so that it can be applied as shown in FIG. 16, also in the same manner discussed above., i.e., after the peelable seal along periphery of edges 5, 5' and 5" have been broken by separating the carrier layer 4b from the liner layer 6b, the initiation of which is shown in FIG. 15. Again in this case the film layer 2b can be eliminated, as in the embodiment of FIGS. 12-14, and this device can thus be used solely for the application of an active agent carrier 15b.

Figure 21:
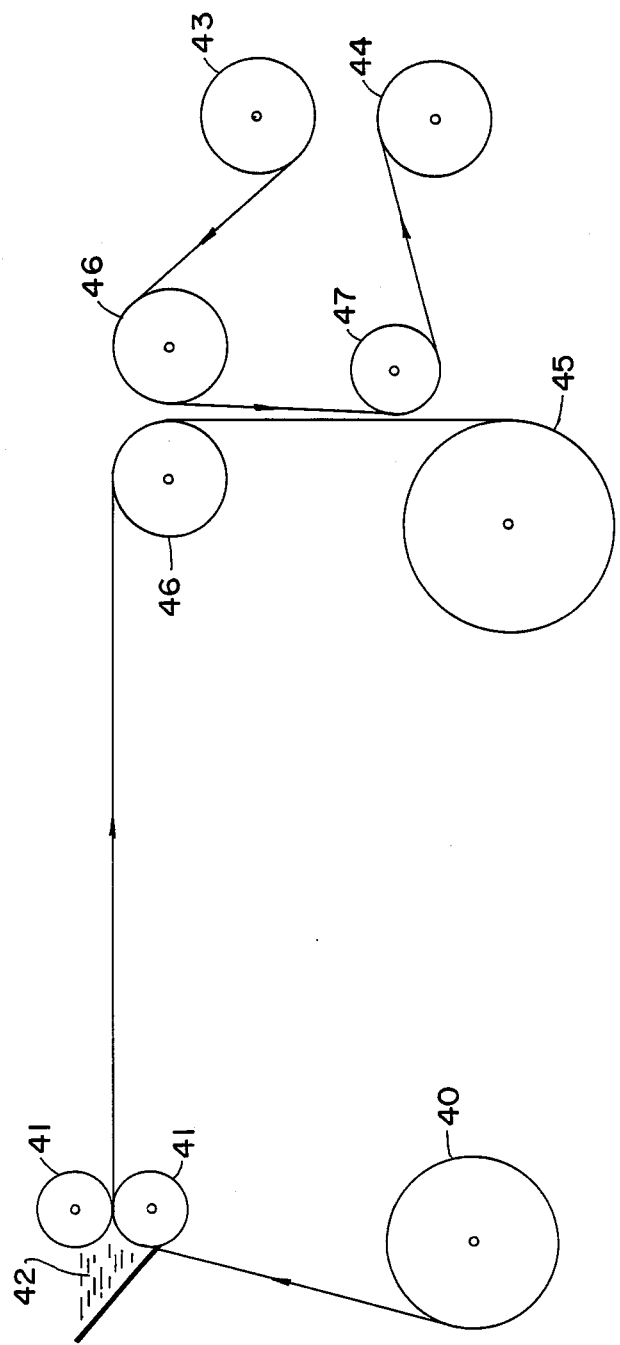
FIG. 21 is a schematic representation of a method for producing a component of a device of the present invention for applying a film layer.
Figure 22:
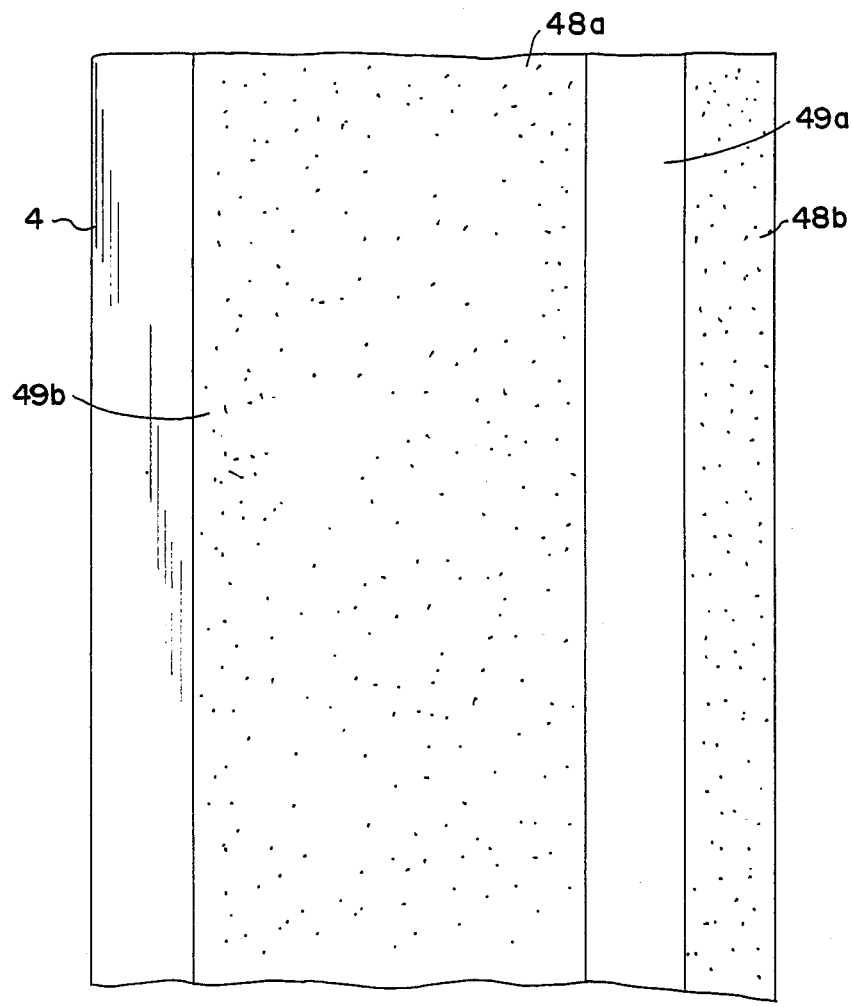
FIG. 22 is a top, elevational view of a portion of the continuous film from which the device of the present invention is produced.
Figure 23:
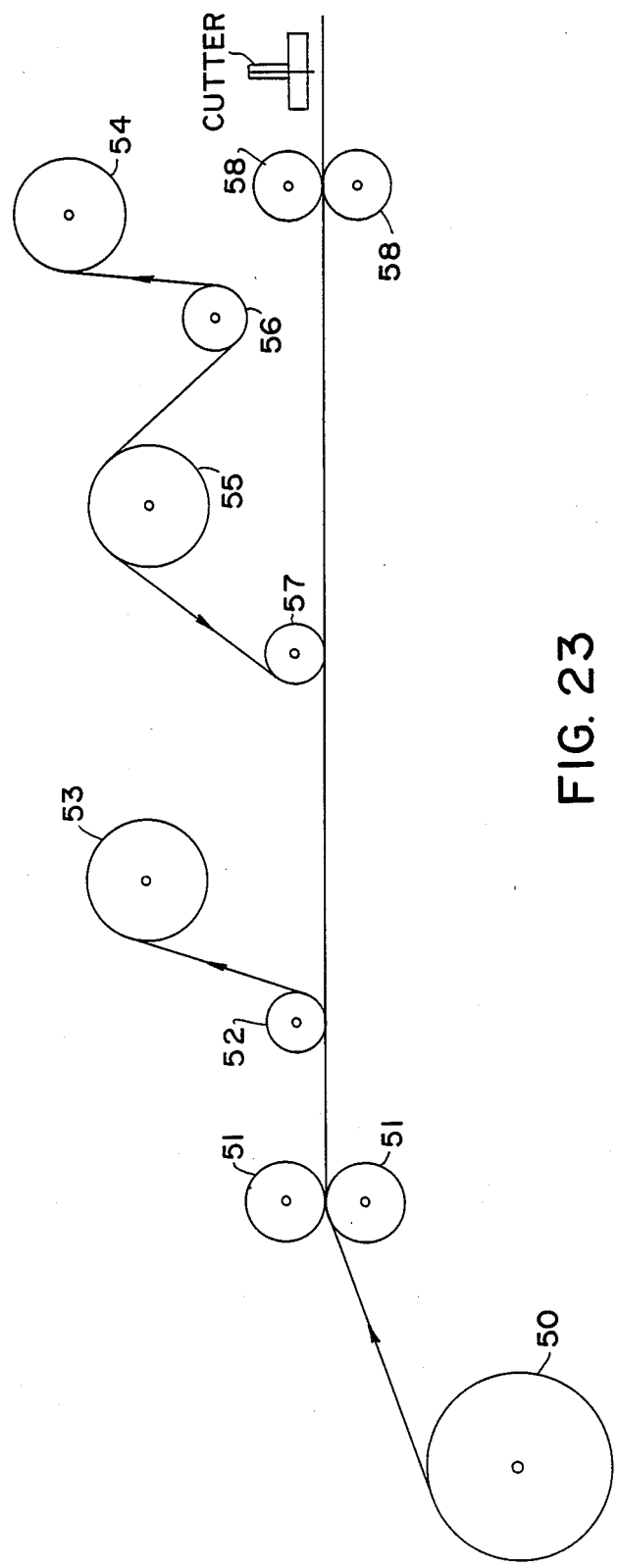
FIG. 23 is a schematic representation of a method for producing a device of the present invention for applying a film layer.

The method of manufacturing the devices of the present invention can be exemplified with respect to production of the embodiment shown in FIGS. 1-8 and with specific reference to FIGS. 21-23 hereof. In this case, the film layer 2 is initially extruded onto a temporary carrier, which can thus act as a release layer such that film layer 2 can be subsequently removed therefrom. This carrier can be a paper backing coated with a silicone release coating or the like, or it can be any such sheet material having appropriate release characteristics for the film layer. The next step in such a manufacturing process comprises providing the liner layer 6, which itself comprises a paper sheet with a silicone or other release coating on its entire surface except for an end strip where no such release coating is applied. This end strip is intended to eventually correspond to the hinge portion 8 of the product. This release coated liner layer 6 is thus unrolled from unwind roll 40, as shown in FIG. 21. Pressure-sensitive adhesive from adhesive supply 42 is then coated onto the release surface of the liner layer 6 at coating station 41, at least onto the portion of the release coating which is intended to correspond to the position of the film layer 2 which will later be applied thereto. At this point the original carrier with the film layer 2 coated thereon is laminated to the upper surface of this adhesive coated onto the release portion of the liner layer 6, and since there is greater adhesion between film layer 2 and the adhesive or liner layer 6 than there is between film layer 2 and the carrier layer, the latter can now be easily removed therefrom, leaving the film layer 2 adhered to the liner layer 6. This is specifically carried out as shown in FIG. 21 by unwinding the temporary carrier with film layer 2 coated thereon from unwinder 43, onto laminating station 46, where it is laminated onto the adhesive coated liner layer 6. The temporary carrier may then be readily removed at idle roller 47, and then wound onto rewinder 44, while the laminate of film layer 2 and liner layer 6 is then wound onto rewinder 45.

Then, in a separate procedure, the carrier layer 4 is prepared. In this case, a temporary release carrier is provided with its entire surface having release characteristics. This carrier is then coated with adhesive, i.e., with an area of adhesive corresponding to adhesive layer 5, and with another separate area of adhesive which corresponds to the hinge area 8, i.e., specifically corresponding to the portion of the liner layer 4 which is not coated with silicone release coating, as discussed above. This carrier layer 4 can be more readily seen in FIG. 22, wherein zone coated areas 48b and 49b represent the areas which are coated with the adhesive. The areas designated 4 and 49a in FIG. 22, on the other hand, represent the non-coated surface of liner layer 4. Thus, the zone coated area 48b corresponds to the adhesive for the hinge 8, while the zone coated area 49b corresponds to the adhesive layer 5. Carrier layer 4, which is paper or the like, is then laminated to the upper face of this carrier layer, with these adhesive zones therebetween. It is also possible to zone coat the adhesive directly onto the surface of carrier layer 4, thus eliminating the need for a separate carrier layer. The carrier layer 4 and liner layers 6 prepared as discussed above are then laminated face-to-face so that the hinge 8 is produced by adhesive joining of the edges of the carrier layer 4 and liner layer 6 where the adhesive strip is located as previously applied to the carrier layer 4, and so that the film layer is now laminated into the position shown in FIGS. 5-8 hereof. Referring specifically to FIG. 23 in this regard, the combination of film layer 2 and liner layer 6 produced in the method shown in FIG. 21 is unwound from unwinder 50, and fed to a die-cutting station 51, where the film layer 2 is cut into its final desired size and shape. Excess portions of the film layer 2 are then removed from the surface of liner layer 6 by means of idle roller 52, and then wound onto rewinder 53. The carrier layer 4 prepared in the manner discussed above is then unwound from unwinder 55, with the temporary carrier removed therefrom via idle roller 56 onto rewinder 54. Thus, the adhesive coated carrier layer 4 is fed onto laminating roller 57 where it is laminated to the die cut film layer 2 carried by liner layer 6. Finally, this overall laminate is fed through sheet rollers 58 to a cutting station to separate individual products from the continuous strip thereof. In the case of the preferred embodiment of the present invention which includes the active agent carrier, this element can readily be incorporated into the above-described method, such as by indexing that element onto the final product upstream of laminating roller 57.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A device for applying a film layer to the skin or mucosa of a patient comprising a liner layer including a first surface and a second surface, said first surface of said liner layer comprising a releasable surface, a carrier layer for said film layer, said carrier layer including a first surface and a second surface, hinge means permanently affixing said first surface of said liner layer to said first surface of said carrier layer at a predetermined location thereon, said film layer being located on said first surface of said carrier layer at a location displaced from said hinge means, first adhesive means interposed between said first surface of said carrier layer and said film layer for maintaining said film layer in contact with said carrier layer when said portion of said carrier layer other than said hinge means is separated from said liner layer, and second adhesive means interposed between said first surface of said liner layer and said first surface of said carrier layer including said film layer, for releasably maintaining said first surface of said carrier layer including said film layer in contact with said first surface of said liner layer, said second adhesive means covering at least the entire periphery of said film layer, said first adhesive means having a first coefficient of adhesion and said second adhesive means having a second coefficient of adhesion, said first coefficient of adhesion of said carrier layer to said film layer being less than said second coefficient of adhesion of said film layer to said skin or mucosa of said patient, whereby upon application of said film layer to said skin or mucosa of said patient with said second adhesive means therebetween, said film layer adheres to said skin or mucosa of said patient and said film layer can simultaneously be removed from said carrier layer.

2. The device of claim 1 wherein said second adhesive means comprises an adhesive layer covering at least the entire surface of said film layer.

3. The device of claim 1 wherein said predetermined location comprises a peripheral edge portion of said liner layer and said carrier layer.

4. The device of claim 1 wherein said hinge means comprises a portion of said liner layer corresponding to said predetermined location being free of said releasable surface, and including adhesive hinge means interposed between said liner layer and said carrier layer at said predetermined location.

5. The device of claim 1 wherein said releasable surface comprises a siliconized coating.

6. The device of claim 1 wherein said liner layer is selected from the group consisting of paper, a thermoplastic, foil, and mixtures thereof.

7. The device of claim 1 wherein a portion of said first surface of said carrier layer in contact with said film layer is free of said first adhesive layer.

8. The device of claim 1 wherein said carrier layer is selected from the group consisting of polyethylene, polypropylene, polyvinylidene chloride, polyethylene terephthalate, polyesters, polyamides, and mixtures thereof.

9. The device of claim 8 wherein said carrier layer comprises polyethylene.

10. The device of claim 1 wherein said film layer is selected from the group consisting of polyether block amides, thermoplastic polyurethanes, and polyesters.

11. The device of claim 1 including removal means for separating said portion of said carrier layer other than said hinge means from said liner layer.

12. The device of claim 11 wherein said removal means comprises an extended portion of said carrier layer extending beyond the edge of said liner layer whereby said extended portion of said carrier layer can be grasped thereby.

13. The device of claim 11 wherein said removal means comprises slit means in said liner layer whereby said liner layer can be grasped at said slit means and separated from said carrier layer.

14. The device of claim 1 wherein said removal means comprises a predetermined peripheral portion of said liner layer being free of said second adhesive layer whereby said liner layer and said carrier layer are not adhesively secured to each other at said predetermined peripheral location and said liner layer and said carrier layer can be grasped therebetween.

15. A device for applying an active agent carrier to the skin or mucosa of a patient comprising a liner layer including a first surface and a second surface, said first surface of said liner layer comprising a releasable surface, a carrier layer for said active agent carrier, said carrier layer including a first surface and a second surface, said active agent carrier being located on said first surface of said carrier layer, first adhesive means interposed between said first surface of said carrier layer and said active agent carrier for maintaining said active agent carrier in contact with said carrier layer when said carrier layer is separated from said liner layer, and second adhesive means interposed between said first surface of said liner layer and said first surface of said carrier layer including said active agent carrier, for releasably maintaining said first surface of said carrier layer including said active agent carrier in contact with said first surface of said liner layer, said second adhesive means covering at least the entire periphery of said active agent carrier, said first adhesive means having a first coefficient of adhesion and said second adhesive layer having a second coefficient of adhesion, said first coefficient of adhesion of said carrier layer to said active agent carrier being less than said second coefficient of adhesion of said active agent carrier to said skin or mucosa of said patient, whereby upon application of said active agent carrier to said skin or mucosa of said patient with said second adhesive means therebetween, said active agent carrier adheres to said skin or mucosa of said patient and said active agent carrier can thereby be removed from said carrier layer.

16. The device of claim 15 wherein said first active agent carrier comprises a reservoir containing said active agent, release means for the controlled release of said active agent from said reservoir, and an active agent impermeable barrier layer between said reservoir and said carrier layer, whereby said active agent may only be released from the inner surface of said reservoir towards said skin or mucosa of said patient upon application of said active agent carrier to said skin or mucosa of said patient.

17. The device of claim 16 wherein said release means comprises an active agent permeable membrane layer formed on said inner surface of said reservoir, whereby said reservoir is completely enclosed between said active agent permeable membrane layer and said active agent impermeable barrier layer.

18. The device of claim 17 wherein said active agent impermeable barrier layer extends peripherally beyond said reservoir about the entire periphery thereof so as to create an extended peripheral area of said active agent impermeable barrier layer.

19. The device of claim 18 wherein said second adhesive means includes an active agent permeable adhesive portion and an active agent impermeable adhesive portion, said active agent permeable adhesive portion corresponding to said active agent permeable membrane layer and said active agent impermeable adhesive portion corresponding to at least said extended peripheral area of said active agent impermeable barrier layer.

20. The device of claim 16 wherein said release means comprises a plurality of micro-capsules containing said active agent encapsulated by an active agent permeable membrane.

21. The device of claim 20 wherein said second adhesive means includes an active agent permeable adhesive portion corresponding to said inner surface of said reservoir.

22. The device of claim 19 wherein said active agent permeable membrane layer extends peripherally beyond said reservoir so as to provide at least a portion of overlapping peripheral surfaces between said peripheral portion of said active agent permeable membrane layer and said peripheral portion of said active agent impermeable barrier layer, and wherein said overlapping peripheral portions are heat sealed together to create an active agent impermeable seal surrounding said reservoir, whereby said active agent impermeable adhesive means is applied to said active agent impermeable seal.

23. A device for applying an active agent carrier to the skin or mucosa of a patient comprising a liner layer including a first surface and a second surface, said first surface of said liner layer comprising a releasable surface, a carrier layer for said active agent carrier, said carrier layer including a first surface and a second surface, hinge means permanently affixing said first surface of said liner layer to said first surface of said carrier layer at a predetermined location thereon, said active agent carrier being located on said first surface of said carrier layer at a location displaced from said hinge means, first adhesive means interposed between said first surface of said carrier layer and said active agent carrier for maintaining said active agent carrier in contact with said carrier layer when said portion of said carrier layer other than said hinge means is separated from said liner layer, and second adhesive means interposed between said first surface of said liner layer and said first surface of said carrier layer including said active agent carrier, for releasably maintaining said first surface of said carrier layer including said active agent carrier in contact with said first surface of said liner layer, said second adhesive means covering at least the entire periphery of said active agent carrier, said first adhesive means having a first coefficient of adhesion and said second adhesive layer having a second coefficient of adhesion, said first coefficient of adhesion of said carrier layer to said active agent carrier being less than said second coefficient of adhesion of said active agent carrier to said skin or mucosa of said patient, whereby upon application of said active agent carrier to said skin or mucosa of said patient with said second adhesive means therebetween, said active agent carrier adheres to said skin or mucosa of said patient and said active agent carrier can thereby be removed from said carrier layer.

24. The device of claim 23 wherein said first active agent carrier comprises a reservoir containing said active agent, release means for the controlled release of said active agent from said reservoir, and an active agent impermeable barrier layer between said reservoir and said carrier layer, whereby said active agent may only be released from the inner surface of said reservoir towards said skin or mucosa of said patient upon application of said active agent carrier to said skin or mucosa of said patient.

25. The device of claim 24 wherein said release means comprises an active agent permeable membrane layer formed on said inner surface of said reservoir, whereby said reservoir is completely enclosed between said active agent permeable membrane layer and said active agent impermeable barrier layer.

26. The device of claim 25 wherein said active agent impermeable barrier layer extends peripherally beyond said reservoir about the entire periphery thereof so as to create an extended peripheral area of said active agent impermeable barrier layer.

27. The device of claim 26 wherein said second adhesive means includes an active agent permeable adhesive portion and an active agent impermeable adhesive portion, said active agent permeable adhesive portion corresponding to said active agent permeable membrane layer and said active agent impermeable adhesive portion corresponding to at least said extended peripheral area of said active agent impermeable barrier layer.

28. The device of claim 24 wherein said release means comprises a plurality of micro-capsules containing said active agent encapsulated by an active agent permeable membrane.

29. The device of claim 28 wherein said second adhesive means includes an active agent permeable adhesive portion corresponding to said inner surface of said reservoir.

30. The device of claim 27 wherein said active agent permeable membrane layer extends peripherally beyond said reservoir so as to provide at least a portion of overlapping peripheral surfaces between said peripheral portion of said active agent permeable membrane layer and said peripheral portion of said active agent impermeable barrier layer, and wherein said overlapping peripheral portions are heat sealed together to create an active agent impermeable seal surrounding said reservoir, whereby said active agent impermeable adhesive means is applied to said active agent impermeable seal.

31. The device of claim 27 wherein said active agent impermeable adhesive layer comprises an adhesive composition selected from the group consisting of natural rubber adhesive, acrylic adhesives, and synthetic adhesives.

32. The device of claim 27 wherein said active agent permeable adhesive layer comprises an adhesive selected from the group consisting of acrylate and methacrylate resins; copolymers of acrylate or methacrylate, esters with acrylic acid, methacrylic acid, acrylamide, methacrylamides, N-alkoxymethyl acrylamides, N-alkoxymethyl methacrylamides, N-t-butylacrylamide, itaconic acid, vinyl acetate, N-branched alkyl maleamic acids wherein the alkyl group has 10 to 24 carbon atoms, glycol diacrylates, or mixture of these monomers; silicon rubber; styrenebutadiene rubber; butylether rubber; neoprene rubber; nitrile rubber; polyisobutylene; polybutadiene; polyisoprene; polyurethane elastomers; polyvinyl alcohol; polyvinyl ethers; polyvinyl pyrrolidone; polyvinyl acetate; ureaformaldehyde resins; phenol formaldehyde resins; resorcinal formaldehyde resins; ethyl cellulose; methyl cellulose; nitrocellulose; cellulose acetate-butyrate; carboxymethyl cellulose; guar gum; acacia gum; pectina gum; starch; destria; gelatin; and casein.

33. The device of claim 25 wherein said active agent permeable membrane layer comprises a material selected from the group consisting of polypropylene, polycarbonates, polyvinyl chloride, cellulose acetate, cellulose nitrate and polyacrylonitrile.

34. The device of claim 23 wherein said active agent impermeable barrier layer comprises a material selected from the group consisting of cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride, paper, cloth and aluminum foil.

35. The device of claim 23 wherein said active agent is selected from the group consisting of scopolamine, nitroglycerine and estradiol.

36. A device for applying a film layer and an active agent carrier to the skin or mucosa of a patient comprising a liner layer including a first surface and a second surface, said first surface of said liner layer comprising a releasable surface, a carrier layer for said film layer and said active agent carrier, said carrier layer including a first surface and a second surface, said film layer including a first surface and a second surface, said first surface of said film layer being located on said first surface of said carrier layer, a first adhesive layer interposed between said first surface of said carrier layer and said first surface of said film layer for maintaining said film layer in contact with said carrier layer when said carrier layer is separated from said liner layer, said active agent carrier being located on said second surface of said film layer, and a second adhesive layer interposed between said first surface of said liner layer and said first surface of said carrier layer including said film layer and said active agent carrier, for releasably maintaining said first surface of said carrier layer including said film layer and said active agent carrier in contact with said first surface of said liner layer, said second adhesive layer covering at least the entire periphery of said film layer, said first adhesive layer having a first coefficient of adhesion and said second adhesive layer having a second coefficient of adhesion, said first coefficient of adhesion of said carrier layer to said film layer being less than said second coefficient of adhesion of said film layer to said skin or mucosa of said patient, whereby upon application of said film layer and said active, agent carrier to said skin or mucosa of said patient with said second adhesive layer therebetween, said film layer and said active agent carrier adhere to said skin or mucosa of said patient and said film layer and said active agent carrier can be simultaneously removed from said carrier layer.

37. The device of claim 36 wherein said active agent carrier comprises a reservoir containing said active agent, release means for the controlled release of said active agent from said reservoir, and an active agent impermeable barrier layer between said reservoir and said film layer, whereby said active agent may only be released from the inner surface of said reservoir towards said skin or mucosa of said patient upon application of said active agent carrier to said skin or mucosa of said patient.

38. The device of claim 37 wherein said release means comprises an active agent permeable membrane layer formed on said inner surface of said reservoir, whereby said reservoir is completely enclosed between said active agent permeable membrane layer and said active agent impermeable barrier layer.

39. The device of claim 38 wherein said active agent impermeable barrier layer extends peripherally beyond said reservoir about the entire periphery thereof so as to create an extended peripheral area of said active agent impermeable barrier layer.

40. The device of claim 39 wherein said second adhesive layer includes an active agent permeable adhesive portion and an active agent impermeable adhesive portion, said active agent permeable adhesive portion corresponding to said active agent permeable membrane layer and said active agent impermeable adhesive portion corresponding to at least said extended peripheral area of said active agent impermeable barrier layer.

41. The device of claim 37 wherein said release means comprises a plurality of micro-capsules containing said active agent encapsulated by an active agent permeable membrane.

42. The device of claim 41 wherein said second adhesive layer includes an active agent permeable adhesive portion corresponding to said inner surface of said reservoir.

43. The device of claim 42 wherein said active agent impermeable barrier layer extends peripherally beyond said reservoir about the entire periphery thereof so as to create an extended peripheral area of said active agent impermeable barrier layer.

44. The device of claim 43 wherein said second adhesive layer includes an active agent impermeable adhesive portion corresponding to at least said extended peripheral area of said active agent impermeable barrier layer.

45. The device of claim 40 wherein said active agent impermeable barrier layer comprises a cover layer including an inner surface and an outer surface, and wherein said active agent impermeable adhesive layer is applied to substantially the entire inner surface of said cover layer.

46. The device of claim 37 wherein said active agent impermeable barrier layer includes an inner surface facing said reservoir, and an outer surface facing said film layer, and a backing member disposed on said portion of said inner surface of said active agent impermeable barrier layer corresponding to said reservoir.

47. The device of claim 40 wherein said active agent permeable membrane layer extends peripherally beyond said reservoir so as to provide at least a portion of overlapping peripheral surfaces between said peripheral portion of said active agent permeable membrane layer and said peripheral portion of said active agent impermeable barrier layer, and wherein said overlapping peripheral portions are heat sealed together to create an active agent impermeable seal surrounding said reservoir, whereby said active agent impermeable adhesive layer is applied to said active agent impermeable seal.

48. The device of claim 44 wherein said active agent impermeable barrier layer comprises a cover layer including an outer surface and an inner surface, and wherein said active agent impermeable adhesive layer is applied to substantially the entire inner surface of said cover layer.

49. A device for applying a film layer and an active agent carrier to the skin or mucosa of a patient comprising a liner layer including a first surface and a second surface, said first surface of said liner layer comprising a releasable surface, a carrier layer for said film layer and said active agent carrier, said carrier layer including a first surface and a second surface, hinge means permanently affixing said first surface of said liner layer to said first surface of said carrier layer at a predetermined location thereon, said film layer including a first surface and a second surface, said first surface of said film layer being located on said first surface of said carrier layer at a location displaced from said hinge means, a first adhesive layer interposed between said first surface of said carrier layer and said first surface of said film layer for maintaining said film layer in contact with said carrier layer when said portion of said carrier layer other than said hinge means is separated from said liner layer, said active agent carrier being located on said second surface of said film layer, and a second adhesive layer interposed between said first surface of said liner layer and said first surface of said carrier layer including said film layer and said active agent carrier, for releasably maintaining said first surface of said carrier layer including said film layer and said active agent carrier in contact with said first surface of said liner layer, said second adhesive layer covering at least the entire periphery of said film layer, said first adhesive layer having a first coefficient of adhesion and said second adhesive layer having a second coefficient of adhesion, said first coefficient of adhesion of said carrier layer to said film layer being less than said second coefficient of adhesion of said film layer to said skin or mucosa of said patient, whereby upon application of said film layer and said active agent carrier to said skin or mucosa of said patient with said second adhesive layer therebetween, said film layer and said active agent carrier adhere to said skin or mucosa of said patient and said film layer and said active agent carrier can be simultaneously removed from aid carrier layer.

50. The device of claim 49 wherein said active agent carrier comprises a reservoir containing said active agent, release means for the controlled release of said active agent from said reservoir, and an active agent impermeable barrier layer between said reservoir and said film layer, whereby said active agent may only be released from the inner surface of said reservoir towards said skin or mucosa of said patient upon application of said active agent carrier to said skin or mucosa of said patient.

51. The device of claim 50 wherein said release means comprises an active agent permeable membrane layer formed on said inner surface of said reservoir, whereby said reservoir is completely enclosed between said active agent permeable membrane layer and said active agent impermeable barrier layer.

52. The device of claim 51 wherein said active agent impermeable barrier layer extends peripherally beyond said reservoir about the entire periphery thereof so as to create an extended peripheral area of said active agent impermeable barrier layer.

53. The device of claim 52 wherein said second adhesive layer includes an active agent permeable adhesive portion and an active agent impermeable adhesive portion, said active agent permeable adhesive portion corresponding to said active agent permeable membrane layer and said active agent impermeable adhesive portion corresponding to at least said extended peripheral area of said active agent impermeable barrier layer.

54. The device of claim 50 wherein said release means comprises a plurality of micro-capsules containing said active agent encapsulated by an active agent permeable membrane.

55. The device of claim 54 wherein said second adhesive layer includes an active agent permeable adhesive portion corresponding to said inner surface of said reservoir.

56. The device of claim 55 wherein said active agent impermeable barrier layer extends peripherally beyond said reservoir about the entire periphery thereof so as to create an extended peripheral area of said active agent impermeable barrier layer.

57. The device of claim 56 wherein said second adhesive layer includes an active agent impermeable adhesive portion corresponding to at least said extended peripheral area of said active agent impermeable barrier layer.

58. The device of claim 53 wherein said active agent impermeable barrier layer comprises a cover layer including an inner surface and an outer surface, and wherein said active agent impermeable adhesive layer is applied to substantially the entire inner surface of said cover layer.

59. The device of claim 50 wherein said active agent impermeable barrier layer includes an inner surface facing said reservoir, and an outer surface facing said film layer, and a backing member disposed on said portion of said inner surface of said active agent impermeable barrier layer corresponding to said reservoir.

60. The device of claim 53 wherein said active agent permeable membrane layer extends peripherally beyond said reservoir so as to provide at least a portion of overlapping peripheral surfaces between said peripheral portion of said active agent permeable membrane layer and said peripheral portion of said active agent impermeable barrier layer, and wherein said overlapping peripheral portions are heat sealed together to create an active agent impermeable seal surrounding said reservoir, whereby said active agent impermeable adhesive layer is applied to said active agent impermeable seal.

61. The device of claim 53 wherein said active agent impermeable adhesive layer comprises an adhesive composition selected from the group consisting of natural rubber adhesive, acrylic adhesives, and synthetic adhesives.

62. The device of claim 53 wherein said active agent permeable adhesive layer comprises an adhesive selected from the group consisting of acrylate and methacrylate resins; copolymers of acrylate or methacrylate, esters with acrylic acid, methacrylic acid, acrylamide, methacrylamides, N-alkoxymethyl acrylamides, N-alkoxymethyl methacrylamides, N-t-butylacrylamide, itaconic acid, vinyl acetate, N-branched alkyl maleamic acids wherein the alkyl group has 10 to 24 carbon atoms, glycol diacrylates, or mixture of these monomers; silicon rubber; styrenebutadiene rubber; butyl-ether rubber; neoprene rubber; nitrile rubber; polyisobutylene; polybutadiene; polyisoprene; polyurethane elastomers; polyvinyl alcohol; polyvinyl ethers; polyvinyl pyrrolidone; polyvinyl acetate; ureaformaldehyde resins; phenol formaldehyde resins; resorcinal formaldehyde resins; ethyl cellulose; methyl cellulose; nitrocellulose; cellulose acetate-butyrate; carboxymethyl cellulose; guar gum; acacia gum; pectina gum; starch; destria; gelatin; and casein.

63. The device of claim 51 wherein said active agent permeable membrane layer comprises a material selected from the group consisting of polypropylene, polycarbonates, polyvinyl chloride, cellulose acetate, cellulose nitrate and polyacrylonitrile.

64. The device of claim 49 wherein said active agent impermeable barrier layer comprises a material selected from the group consisting of cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride, paper, cloth and aluminum foil.

65. The device of claim 58 wherein said cover layer is selected from the group consisting of a film of polyethylene terephthalate on polyethylene or a polyethylene/metallized polyethylene terephthalate/ polyethylene laminate.

66. The device of claim 49 wherein said active agent is selected from the group consisting of scopolamine, nitroglycerine and estradiol.

67. The device of claim 57 wherein said active agent impermeable barrier layer comprises a cover layer including an outer surface and an inner surface, and wherein said active agent impermeable adhesive layer is applied to substantially the entire inner surface of said cover layer.

68. The device of claim 61 wherein said active agent impermeable adhesive layer comprises an adhesive composition selected from the group consisting of natural rubber adhesives, acrylic adhesives, and synthetic adhesives.

69. The device of claim 57 wherein said active agent permeable adhesive layer comprises an adhesive selected from the group consisting of acrylate and methacrylate resins; copolymers of acrylate or methacrylate esters with acrylic acid, methacrylic acid, acrylamide, methacrylamides, N-alkoxymethyl acrylamides, N-alkoxymethyl methacrylamides, N-t-butylacrylamide, itaconic acid, vinylacetate, N-branched N-branched alkyl maleamic acids wherein the alkyl group has 10 to 24 carbon atoms, glycol diacrylates, or mixture of these monomers; silicon rubber; styrene-butadiene rubber; butyl-ether rubber; neoprene rubber; nitrile rubber; polyisobutylene; polybutadiene; polyisoprene; polyurethane elastomers; polyvinyl alcohol; polyvinyl ethers; polyvinyl pyrrolidone; polyvinyl acetate; ureaformaldehyde resins; phenol formaldehyde resins; resorcinal formaldehyde resins; ethyl cellulose; methyl cellulose; nitrocellulose; cellulose acetate-butyrate; carboxymethyl cellulose; guar gum; acacia gum; pectina gum; starch; destria; gelatin; and casein.

70. The device of claim 50 wherein said active agent permeable membrane layer is selected from the group consisting of polyvinyl chloride either unplasticized or plasticized with long-chain fatty amides, plasticized nylon, unplasticized soft nylon, silicone rubber, polyethylene, polyethylene terephthalate, polymerized esters of acrylic and methacrylic acid, modified collagent, cross-linked hydrophilic polyether gels, cross-linked polyvinyl alcohol, cross-linked partially hydrolyzed polyvinyl acetate, methyl cellulose, ethyl cellulose, hydroxyethyl cellulose, acacia gum, carboxymethyl cellulose, and carageenan alone or combined with gelatin.

71. The device of claim 48 wherein said cover layer is selected from the group consisting of a film of polyethylene terephthalate or polyethylene or a polyethylene/metallized polyethylene terephthalate/ polyethylene laminate.

72. A device for applying a film layer to the skin or mucosa of a patient comprising a liner layer including a first surface and a second surface, said first surface of said liner layer comprising a releasable surface, a carrier layer for said film layer, said carrier layer including a first surface and a second surface, said liner layer and said film layer having corresponding outer peripheries, said film layer being located on said first surface of said carrier layer, temporary closure means for temporarily sealing said first surface of said liner layer to said first surface of said carrier layer at at least a portion of the corresponding outer peripheries thereof so as to provide a sealed container for said film layer therein, said temporary closure means comprising a peelable heat seal formed between said first surface of said liner layer and said first surface of said carrier layer, a first adhesive layer interposed between said first surface of said carrier layer and said film layer for maintaining said film layer in contact with said carrier layer when said temporary closure means is unsealed and said carrier layer is separated from said liner layer, and a second adhesive layer interposed between said first surface of said liner layer and said first surface of said carrier layer including said film layer for releasably maintaining said first surface of said carrier layer including said film layer in contact with said first surface of said film layer in contact with said first surface of said liner layer, said second adhesive layer covering at least the entire periphery of said film layer, said first adhesive layer having a first coefficient of adhesion and said second adhesive layer having a second coefficient of adhesion, said first coefficient of adhesion of said carrier layer to said film layer being less than said second coefficient of adhesion of said film layer to said skin or mucosa of said patient, whereby upon application of said film layer to said skin or mucosa of said patient with said second adhesive layer therebetween, said film layer adheres to said skin or mucosa of said patient and said film layer can simultaneously be removed from said carrier layer.

73. The device of claim 72 wherein said first surface of said liner layer comprises a first polymer layer and said first surface of said carrier layer comprises a second polymer layer, and wherein said first and second polymer layers comprise different polymers whereby said peelable heat seal is formed therebetween.

74. The device of claim 72 wherein said releasable surface comprises a siliconized coating.

75. The device of claim 74 wherein said first surface of said liner layer comprises a first polymer layer and said first surface of said carrier layer comprises a second polymer layer.

76. The device of claim 75 wherein said first and second polymer layers comprise the same polymer.

77. The device of claim 72 wherein said first surface of said liner layer comprises a first polymer layer, said second surface of said liner layer comprises a paper layer, and said liner layer includes an intermediate layer between said first surface and said second surface, said intermediate layer comprising a metallized film layer.

78. The device of claim 77 wherein said first surface of said carrier layer comprises a first polymer layer, said second surface of said carrier layer comprises a paper layer, and said carrier layer includes an intermediate layer between said first surface and said second surface, said intermediate layer comprising a metallized film layer.

79. The device of claim 78 wherein said temporary closure means comprises a peelable heat seal formed between said first surface of said liner layer and said first surface of said carrier layer.

80. The device of claim 79 wherein said first surface of said carrier layer comprises a first polymer layer, said second surface of said carrier layer comprises a paper layer, and said carrier layer includes an intermediate layer between said first surface and said second surface of the carrier layer, said intermediate layer comprising a metallized film layer.

81. A device for applying a film layer to the skin or mucosa of a patient comprising a liner layer including a first surface and a second surface, said first surface of said liner layer comprising a releasable surface, a carrier layer for said film layer, said carrier layer including a first surface and a second surface, said liner layer and said film layer having corresponding outer peripheries, hinge means permanently affixing said first surface of said liner layer to said first surface of said carrier layer at a predetermined location comprising a portion of said corresponding outer peripheries thereof, said film layer being located on said first surface of said carrier layer at a location displaced from said hinge means, temporary closure means for temporarily sealing said first surface of said liner layer to said first surface of said carrier layer at the remaining portion of said corresponding outer peripheries thereof so as to provide a sealed container for said film layer therein, a first adhesive layer interposed between said first surface of said carrier layer and said film layer for maintaining said film layer in contact with said carrier layer when said temporary closure means is unsealed and said portion of said carrier layer other than said hinge means is separated from said liner layer, and a second adhesive layer interposed between said first surface of said liner layer and said first surface of said carrier layer including said film layer for releasably maintaining said first surface of said carrier layer including said film layer in contact with said first surface of said film layer in contact with said first surface of said liner layer, said second adhesive layer covering at least the entire periphery of said film layer, said first adhesive layer having a first coefficient of adhesion and said second adhesive layer having a second coefficient of adhesion, said first coefficient of adhesion of said carrier layer to said film layer being less than said second coefficient of adhesion of said film layer to said skin or mucosa of said patient, whereby upon application of said film layer to said skin or mucosa of said patient with said second adhesive layer therebetween, said film layer adheres to said skin or mucosa of said patient and said film layer can simultaneously be removed from said carrier layer.

82. The device of claim 81 wherein said temporary closure means comprises a peelable heat seal formed between said first surface of said liner layer and said first surface of said carrier layer.

83. The device of claim 82 wherein said first surface of said liner layer comprises a first polymer layer and said first surface of said carrier layer comprises a second polymer layer, and wherein said first and second polymer layers comprise different polymers whereby said peelable heat seal is formed therebetween.

84. The device of claim 82 wherein said releasable surface comprises a siliconized coating.

85. The device of claim 84 wherein said first surface of said liner layer comprises a first polymer layer and said first surface of said carrier layer comprises a second polymer layer.

86. The device of claim 85 wherein said first and second polymer layers comprise the same polymer.

87. The device of claim 82 wherein said first surface of said liner layer comprises a first polymer layer, said second surface of said liner layer comprises a paper layer, and said liner layer includes an intermediate layer between said first surface and said second surface, said intermediate layer comprising a metallized film layer.

88. The device of claim 87 wherein said first surface of said carrier layer comprises a first polymer layer, said second surface of said carrier layer comprises a paper layer, and said carrier layer includes an intermediate layer between said first surface and said second surface, said intermediate layer comprising a metallized film layer.

89. The device of claim 88 wherein said temporary closure means comprises a peelable heat seal formed between said first surface of said liner layer and said first surface of said carrier layer.

90. The device of claim 89 wherein said liner layer and said carrier layer each has a substantially square configuration, wherein said predetermined location for said hinge means comprises a first side of said square, and wherein said temporary closure means is located at the second, third and fourth sides of said square.

91. The device of claim 90 wherein said first surface of said liner layer comprises a first polymer layer and said second surface of said carrier layer comprises a second polymer layer, and said first and second polymer layers comprise different polymers whereby said peelable heat seal is formed therebetween.

92. The device of claim 90 wherein said releasable surface comprises a siliconized coating.

93. The device of claim 92 wherein said first surface of said liner layer comprises a first polymer layer and said first surface of said carrier layer comprises a second polymer layer.

94. The device of claim 93 wherein said first and second polymer layers comprise the same polymer.

95. The device of claim 90 wherein said first surface of said liner layer comprises a first polymer layer, said second surface of said liner layer comprises a paper layer, and said liner layer includes an intermediate layer between said first surface and said second surface, said intermediate layer comprising a metallized film layer.

96. The device of claim 89 wherein said first surface of said carrier layer comprises a first polymer layer, said second surface of said carrier layer comprises a paper layer, and said carrier layer includes an intermediate layer between said first surface and said second surface of the carrier layer, said intermediate layer comprising a metallized film layer.

97. A device for applying a film layer and an active agent carrier to the skin or mucosa of a patient comprising a liner layer including a first surface and a second surface, said first surface of said liner layer comprising a releasable surface, a carrier layer for said film layer and said active agent carrier, said carrier layer including a first surface and a second surface, said liner layer and said film layer having corresponding outer peripheries, said film layer including a first surface and a second surface, and said first surface of said film layer being located on said first surface of said carrier layer, temporary closure means for temporarily sealing said first surface of said liner layer to said first surface of said liner layer to said first surface of said carrier layer at at least a portion of said corresponding outer peripheries thereof, so as to provide a sealed container for said film layer and said active agent carrier therein, a first adhesive layer interposed between said first surface of said carrier layer and said first surface of said film layer for maintaining said film layer in contact with said carrier layer when said temporary closure means is unsealed and said portion of said carrier layer other than said hinge means is separated from said liner layer, and a second adhesive layer interposed between said first surface of said liner layer and said first surface of said carrier layer including said film layer and said active agent carrier for releasably maintaining said first surface of said carrier layer including said film layer and said active agent carrier in contact with said first surface of said liner layer, said second adhesive layer covering at least the entire periphery of said film layer, said first adhesive layer having a first coefficient of adhesion and said second adhesive layer having a second coefficient of adhesion, said first coefficient of adhesion of said carrier layer to said film layer being less than said second coefficient of adhesion of said film layer to said skin or mucosa of said patient, whereby upon application of said film layer and said active agent carrier to said skin or mucosa of said patient with said second adhesive layer therebetween, said film layer and said active agent carrier adhere to said skin or mucosa of said patient and said film layer and said active agent carrier can simultaneously be removed from said carrier layer.

98. The device of claim 97 wherein said active agent carrier comprises a reservoir containing said active agent, release means for the controlled release of said active agent from said reservoir, and an active agent impermeable barrier layer between said reservoir and said film layer, whereby said active agent may only be released from the inner surface of said reservoir towards said skin or mucosa of said patient upon application of said film layer and said active agent carrier to said skin or mucosa of said patient.

99. The device of claim 98 wherein said release means comprises an active agent permeable membrane layer formed on said inner surface of said reservoir, whereby said reservoir is completely enclosed between said active agent permeable membrane layer and said active agent impermeable barrier layer.

100. The device of claim 99 wherein said active agent impermeable barrier layer extends peripherally beyond said reservoir about the entire periphery thereof so as to create an extended peripheral area of said active agent impermeable barrier layer.

101. The device of claim 100 wherein said second adhesive layer includes an active agent permeable adhesive portion and an active agent impermeable adhesive portion, said active agent permeable adhesive portion corresponding to said active agent permeable membrane layer and said active agent impermeable adhesive portion corresponding to at least said extended peripheral area of said active agent impermeable barrier layer.

102. The device of claim 98 wherein said release means comprises a plurality of micro-capsules containing said active agent encapsulated by an active agent permeable membrane.

103. The device of claim 102 wherein said second adhesive layer includes an active agent permeable adhesive portion corresponding to said inner surface of said reservoir.

104. The device of claim 103 wherein said active agent impermeable barrier layer extends peripherally beyond said reservoir about the entire periphery thereof so as to create an extended peripheral area of said active agent impermeable barrier layer.

105. The device of claim 104 wherein said second adhesive layer includes an active agent impermeable adhesive portion corresponding to at least said extended peripheral area of said active agent impermeable barrier layer.

106. The device of claim 101 wherein said active agent impermeable barrier layer comprises a cover layer including an inner surface and an outer surface, and wherein said active agent impermeable adhesive layer is applied to substantially the entire inner surface of said cover layer.

107. The device of claim 101 wherein said active agent permeable membrane layer extends peripherally beyond said reservoir so as to provide at least a portion of overlapping peripheral surfaces between said peripheral portion of said active agent permeable membrane layer and said peripheral portion of said active agent impermeable barrier layer, and wherein said overlapping peripheral portions are heat sealed together to create an active agent impermeable seal surrounding said reservoir, whereby said active agent impermeable adhesive layer is applied to said active agent impermeable seal.

108. The device of claim 105 wherein said active agent impermeable barrier layer comprises a cover layer including an outer surface and an inner surface, and wherein said active agent impermeable adhesive layer is applied to substantially the entire inner surface of said cover layer.

109. The device of claim 97 wherein said temporary closure means comprises a peelable heat seal formed between said first surface of said liner layer and said first surface of said carrier layer.

110. The device of claim 109 wherein said first surface of said liner layer comprises a first polymer layer and said first surface of said carrier layer comprises a second polymer layer, and wherein said first and second polymer layers comprise different polymers whereby said peelable heat seal is formed therebetween.

111. The device of claim 109 wherein said releasable surface comprises a siliconized coating.

112. The device of claim 111 wherein said first surface of said liner layer comprises a first polymer layer and said first surface of said carrier layer comprises a second polymer layer.

113. The device of claim 112 wherein said first and second polymer layers comprise the same polymer.

114. The device of claim 110 wherein said first surface of said liner layer comprises a first polymer layer, said second surface of said liner layer comprises a paper layer, and said liner layer includes an intermediate layer between said first surface and said second surface, said intermediate layer comprising a metallized film layer.

115. The device of claim 114 wherein said first surface of said carrier layer comprises a first polymer layer, said second surface of said carrier layer comprises a paper layer, and said carrier layer includes an intermediate layer between said first surface and said second surface, said intermediate layer comprising a metallized film layer

116. The device of claim 115 wherein said temporary closure means comprises a peelable heat seal formed between said first surface of said liner layer and said first surface of said carrier layer

117. A device for applying a film layer and an active agent carrier to the skin or mucosa of a patient comprising a liner layer including a first surface and a second surface, said first surface of said liner layer comprising a releasable surface, a carrier layer for said film layer and said active agent carrier, said carrier layer including a first surface and a second surface, said liner layer and said film layer having corresponding outer peripheries, hinge means permanently affixing said first surface of said liner layer to said first surface of said carrier layer at a predetermined location comprising a portion of said corresponding outer peripheries thereof, said film layer including a first surface and a second surface, and said first surface of said film layer being located on said first surface of said carrier layer at a location displaced from said hinge means, temporary closure means for temporarily sealing said first surface of said liner layer to said first surface of said liner layer to said first surface of said carrier layer at the remaining portion of said corresponding outer peripheries thereof, so as to provide a sealed container for said film layer and said active agent carrier therein, a first adhesive layer interposed between said first surface of said carrier layer and said first surface of said film layer for maintaining said film layer in contact with said carrier layer when said temporary closure means is unsealed and said portion of said carrier layer other than said hinge means is separated from said liner layer, and a second adhesive layer interposed between said first surface of said liner layer and said first surface of said carrier layer including said film layer and said active agent carrier for releasably maintaining said first surface of said carrier layer including said film layer and said active agent carrier in contact with said first surface of said liner layer, said second adhesive layer covering at least the entire periphery of said film layer, said first adhesive layer having a first coefficient of adhesion and said second adhesive layer having a second coefficient of adhesion, said first coefficient of adhesion of said carrier layer to said film layer being less than said second coefficient of adhesion of said film layer to said skin or mucosa of said patient, whereby upon application of said film layer and said active agent carrier to said skin or mucosa of said patient with said second adhesive layer therebetween, said film layer and said active agent carrier adhere to said skin or mucosa of said patient and said film layer and said active agent carrier can simultaneously be removed from said carrier layer.

118. The device of claim 117 wherein said active agent carrier comprises a reservoir containing said active agent, release means for the controlled release of said active agent from said reservoir, and an active agent impermeable barrier layer between said reservoir and said film layer, whereby said active agent may only be released from the inner surface of said reservoir towards said skin or mucosa of said patient upon application of aid film layer and said active agent carrier to said skin or mucosa of said patient.

119. The device of claim 118 wherein said release means comprises an active agent permeable membrane layer formed on said inner surface of said reservoir, whereby said reservoir is completely enclosed between said active agent permeable membrane layer and said active agent impermeable barrier layer.

120. The device of claim 119 wherein said active agent impermeable barrier layer extends peripherally beyond said reservoir about the entire periphery thereof so as to create an extended peripheral area of said active agent impermeable barrier layer.

121. The device of claim 120 wherein said second adhesive layer includes an active agent permeable adhesive portion and an active agent impermeable adhesive portion, said active agent permeable adhesive portion corresponding to said active agent permeable membrane layer and said active agent impermeable adhesive portion corresponding to at least said extended peripheral area of said active agent impermeable barrier layer.

122. The device of claim 119 wherein said release means comprises a plurality of micro-capsules containing said active agent encapsulated by an active agent permeable membrane.

123. The device of claim 122 wherein said second adhesive layer includes an active agent permeable adhesive portion corresponding to said inner surface of said reservoir.

124. The device of claim 123 wherein said active agent impermeable barrier layer extends peripherally beyond said reservoir about the entire periphery thereof so as to create an extended peripheral area of said active agent impermeable barrier layer.

125. The device of claim 124 wherein said second adhesive layer includes an active agent impermeable adhesive portion corresponding to at least said extended peripheral area of said active agent impermeable barrier layer.

126. The device of claim 121 wherein said active agent impermeable barrier layer comprises a cover layer including an inner surface and an outer surface, and wherein said active agent impermeable adhesive layer is applied to substantially the entire inner surface of said cover layer.

127. The device of claim 121 wherein said active agent permeable membrane layer extends peripherally beyond said reservoir so as to provide at least a portion of overlapping peripheral surfaces between said peripheral portion of said active agent permeable membrane layer and said peripheral portion of said active agent impermeable barrier layer, and wherein said overlapping peripheral portions are heat sealed together to create an active agent impermeable seal surrounding said reservoir, whereby said active agent impermeable adhesive layer is applied to said active agent impermeable seal.

128. The device of claim 121 wherein said active agent impermeable adhesive layer comprises an adhesive composition selected from the group consisting of natural rubber adhesive, acrylic adhesives, and synthetic adhesives.

129. The device of claim 121 wherein said active agent permeable adhesive layer comprises an adhesive selected from the group consisting of acrylate and methacrylate resins; copolymers of acrylate or methacrylate, esters with acrylic acid, methacrylic acid, acrylamide, methacrylamides, N-alkoxymethyl acrylamides, N-alkoxymethyl methacrylamides, N-t-butylacrylamide, itaconic acid, vinyl acetate, N-branched alkyl maleamic acids wherein the alkyl group has 10 to 24 carbon atoms, glycol diacrylates, or mixture of these monomers; silicon rubber; styrenebutadiene rubber; butyl-ether rubber; neoprene rubber; nitrile rubber; polyisobutylene; polybutadiene; polyisoprene; polyurethane elastomers; polyvinyl alcohol; polyvinyl ethers; polyvinyl pyrrolidone; polyvinyl acetate; ureaformaldehyde resins; phenol formaldehyde resins; resorcinal formaldehyde resins; ethyl cellulose; methyl cellulose; nitrocellulose; cellulose acetate-butyrate; carboxymethyl cellulose; guar gum; acacia gum; pectina gum; starch; destria; gelatin; and casein.

130. The device of claim 119 wherein said active agent permeable membrane layer comprises a material selected from the group consisting of polypropylene, polycarbonates, polyvinyl chloride, cellulose acetate, cellulose nitrate and polyacrylonitrile.

131. The device of claim 117 wherein said active agent impermeable barrier layer comprises a material selected from the group consisting of cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride, paper, cloth and aluminum foil.

132. The device of claim 126 wherein said cover layer is selected from the group consisting of a film of polyethylene terephthalate on polyethylene or a polyethylene/metallized polyethylene terephthalate/ polyethylene laminate.

133. The device of claim 117 wherein said active agent is selected from the group consisting of scopolamine, nitroglycerine and estradiol.

134. The device of claim 125 wherein said active agent impermeable barrier layer comprises a cover layer including an outer surface and an inner surface, and wherein said active agent impermeable adhesive layer is applied to substantially the entire inner surface of said cover layer.

135. The device of claim 125 wherein said active agent impermeable adhesive layer comprises an adhesive composition selected from the group consisting of natural rubber adhesives, acrylic adhesives, and synthetic adhesives.

136. The device of claim 125 wherein said active agent permeable adhesive layer comprises an adhesive selected from the group consisting of acrylate and methacrylate resins; copolymers of acrylate or methacrylate esters with acrylic acid, methacrylic acid, acrylamide, methacrylamides, N-alkoxymethyl acrylamides, N-alkoxymethyl methacrylamides, N-t-butylacrylamide, itaconic acid, vinylacetate, N-branched N-branched alkyl maleamic acids wherein the alkyl group has 10 to 24 carbon atoms, glycol diacrylates, or mixture of these monomers; silicon rubber; styrene-butadiene rubber; butyl-ether rubber; neoprene rubber; nitrile rubber; polyisobutylene; polybutadiene; polyisoprene; polyurethane elastomers; polyvinyl alcohol; polyvinyl ethers; polyvinyl pyrrolidone; polyvinyl acetate; urea-formaldehyde resins; phenol formaldehyde resins; resorcinal formaldehyde resins; ethyl cellulose; methyl cellulose; nitrocellulose; cellulose acetate-butyrate; carboxymethyl cellulose; guar gum; acacia gum; pectina gum; starch; destria; gelatin; and casein.

137. The device of claim 119 wherein said active agent permeable membrane layer is selected from the group consisting of polyvinyl chloride either unplasticized or plasticized with long-chain fattyamides, plasticized nylon, unplasticized soft nylon, silicone rubber, polyethylene, polyethylene terephthalate, polymerized esters of acrylic and methacrylic acid, modified collagent, cross-linked hydrophilic polyether gels, cross-linked polyvinyl alcohol, cross-linked partially hydrolyzed polyvinyl acetate, methyl cellulose, ethyl cellulose, hydroxyethyl cellulose, acacia gum, carboxymethyl cellulose, and carageenan alone or combined with gelatin.

138. The device of claim 126 wherein said cover layer is selected from the group consisting of a film of polyethylene terephthalate or polyethylene or a polyethylene/metallized polyethylene terephthalate/ polyethylene laminate.

139. The device of claim 118 wherein said temporary closure means comprises a peelable heat seal formed between said first surface of said liner layer and said first surface of said carrier layer.

140. The device of claim 134 wherein said first surface of said liner layer comprises a first polymer layer and said first surface of said carrier layer comprises a second polymer layer, and wherein said first and second polymer layers comprise different polymers whereby said peelable heat seal is formed therebetween.

141. The device of claim 134 wherein said releasable surface comprises a siliconized coating.

142. The device of claim 141 wherein said first surface of said liner layer comprises a first polymer layer and said first surface of said carrier layer comprises a second polymer layer.

143. The device of claim 142 wherein said first and second polymer layers comprise the same polymer.

144. The device of claim 135 wherein said first surface of said liner layer comprises a first polymer layer, said second surface of said liner layer comprises a paper layer, and said liner layer includes an intermediate layer between said first surface and said second surface, said intermediate layer comprising a metallized film layer.

145. The device of claim 144 wherein said first surface of said carrier layer comprises a first polymer layer, said second surface of said carrier layer comprises a paper layer, and said carrier layer includes an intermediate layer between said first surface and said second surface, said intermediate layer comprising a metallized film layer.

146. The device of claim 145 wherein said temporary closure means comprises a peelable heat seal formed between said first surface of said liner layer and said first surface of said carrier layer.

147. The device of claim 146 wherein said liner layer and said carrier layer each has a substantially square configuration, wherein said predetermined location for said hinge means comprises a first side of said square, and wherein said temporary closure means is located at the second, third and fourth sides of said square.

148. The device of claim 147 wherein said first surface of said liner layer comprises a first polymer layer and said second surface of said carrier layer comprises a second polymer layer, and wherein said first and second polymer layers comprise different polymers whereby said peelable heat seal is formed therebetween.

149. The device of claim 147 wherein said releasable surface comprises a siliconized coating.

150. The device of claim 149 wherein said first surface of said liner layer comprises a first polymer layer and said first surface of said carrier layer comprises a second polymer layer.

151. The device of claim 150 wherein said first and second polymer layers comprise the same polymer.

152. The device of claim 147 wherein said first surface of said liner layer comprises a first polymer layer, said second surface of said liner layer comprises a paper layer, and said liner layer includes an intermediate layer between said first surface and said second surface, said intermediate layer comprising a metallized film layer.

153. The device of claim 142 wherein said first surface of said carrier layer comprises a first polymer layer, said second surface of said carrier layer comprises a paper layer, and said carrier layer includes an intermediate layer between said first surface and said second surface of the carrier layer, said intermediate layer comprising a metallized film layer.

* * * * *

UNITED STATES PATENT AND TRADEMARK OFFICE
CERTIFICATE OF CORRECTION

PATENT NO. : 4,915,102

DATED : April 10, 1990

INVENTOR(S) : Alfred Kwiatek, et al

It is certified that error appears in the above-identified patent and that said Letters Patent is hereby corrected as shown below:

Column 37, line 31, delete "portion of said".
           lines 31 and 32, delete "other than said hinge means".
Column 37, lines 22-23, delete --said first surface of the liner layer--(2nd occurrence)

Signed and Sealed this

Thirteenth Day of October, 1992

Attest:

DOUGLAS B. COMER

*Attesting Officer*       *Acting Commissioner of Patents and Trademarks*